(12) United States Patent
Kubota et al.

(10) Patent No.: US 8,137,914 B2
(45) Date of Patent: Mar. 20, 2012

(54) VARIANTS OF ALPHA-FETOPROTEIN CODING AND EXPRESSION SEQUENCES

(75) Inventors: Hiroshi Kubota, Chapel Hill, NC (US); Lola M. Reid, Chapel Hill, NC (US); Robert Storms, Durham, NC (US)

(73) Assignee: University of North Carolina at Chapel Hill, Chapel Hill, NC (US)

( * ) Notice: Subject to any disclaimer, the term of this patent is extended or adjusted under 35 U.S.C. 154(b) by 806 days.

(21) Appl. No.: 11/963,207

(22) Filed: Dec. 21, 2007

(65) Prior Publication Data

US 2008/0131900 A1 Jun. 5, 2008

Related U.S. Application Data

(62) Division of application No. 10/254,676, filed on Sep. 26, 2002, now Pat. No. 7,332,589.

(60) Provisional application No. 60/324,540, filed on Sep. 26, 2001.

(51) Int. Cl.
*C12Q 1/68* (2006.01)
*C12N 15/11* (2006.01)
*C12P 19/34* (2006.01)

(52) U.S. Cl. ....... 435/6.11; 435/91.2; 435/6; 536/24.33; 536/24.31

(58) Field of Classification Search .................. None
See application file for complete search history.

(56) References Cited

U.S. PATENT DOCUMENTS

| 5,955,594 | A * | 9/1999 | Mishra | 536/23.5 |
| 2002/0039786 | A1 | 4/2002 | Reid et al. | |
| 2002/0182188 | A1 | 12/2002 | Reid et al. | |
| 2003/0175702 | A1 | 9/2003 | Schweitzer et al. | |
| 2005/0003529 | A1 | 1/2005 | Taniguchi et al. | |
| 2005/0148072 | A1 | 7/2005 | Reid et al. | |

OTHER PUBLICATIONS

Smith et al., "The challenges of genome sequence annotation or "The devil is in the details"," *Nature Biotechnology*, Nov. 1997, pp. 1222-1223, vol. 15.
Tseng et al., "Evolutionary model for predicting protein function by matching local surfaces: a Bayesian monte Carloapproach," poster abstract downloaded Jun. 9, 2005.
Wiethege et al., *Pathol. Res. Pract.*, 1991, 187:912-915.
Wulf et al., *Biotechniques*, 1995, pp. 368-372, vol. 19, No. 3.

* cited by examiner

*Primary Examiner* — Maria Marvich
(74) *Attorney, Agent, or Firm* — Gilberto M. Villacorta; Sunit Talapatra; Foley & Lardner LLP

(57) ABSTRACT

The invention discloses the sequences of variant forms of alpha-fetoprotein transcripts that have been identified in human hemopoietic progenitors but not in differentiated mature cells. The variant forms of AFP (vAFP) cDNA sequences isolated from a multipotent hemopoietic cell line, K562, differ from the authentic AFP transcript, consisting of 15 exons, by lacking only exon 1. Instead of exon 1, vAFP transcripts use an additional one or two exons located in the 5'-untranslated region of the AFP gene. K562 expressed selectively vAFP, whereas a hepatocellular carcinoma cell line, HepG2, showed no detectable expression of vAFP. In normal adult tissues, vAFP transcripts is detected in the bone marrow, thymus and brain, but not the spleen, suggesting the expression occurs in normal hemopoietic progenitors. Moreover, CD34+Lin– hemopoietic stem/progenitor cells purified by flow cytometric sorting also express the variant transcripts.

5 Claims, 7 Drawing Sheets

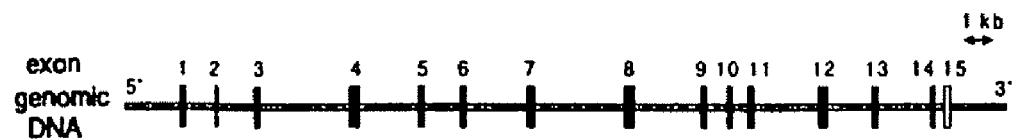
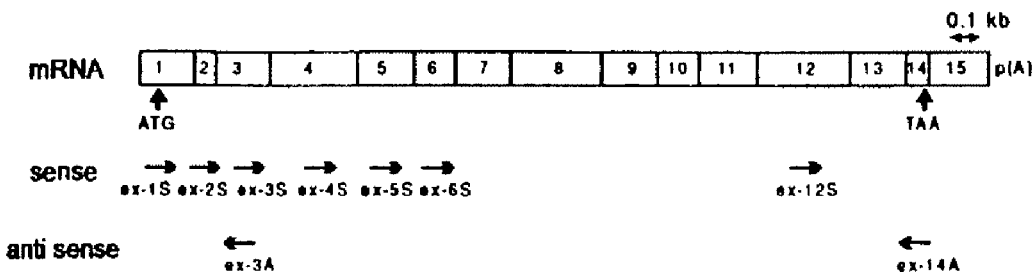
FIGURE 1

A

```
               ←─────────────── exon A ───────────────────────────────
TTTCTTAAGAATTAAGGGACAGACTATGGGCTGGAGGACTTTGAGGATGTCTGTCTCATA
                         GACTATGGGCTGGAGGACTTTGAGGATGTCTGTCTCATA
_____

ACACTTGGGTTGTATCTGTTCTATGGGGCTTGTTTTAAGCTTGGCAACTTGCAACAGGGT
ACACTTGGGTTGTATCTGTTCTATGGGGCTTGTTTTAAGCTTGGCAACTTGCAACAGGGT
_____ >|< ────────── exon B ───────
TCACTGACTTTCTCCCCAGGCCCAAG-----------------------------------
TCACTGACTTTCTCCCCAGGCCCAAGGTATTCCTTCATAACAAATACTTTGGCTTTCATA
_____

-------------------------------------------------------------
TATTTGAGTAAAGTCCCCCTTGAGGAAGAGTAGAAGAACTGCACTTTGTAAATACTATCC
                                              >|< ────── exon 2
---------------------------------------------:-CTTCCATATTGGA
TGGAATCCAAACGGATAGACAAGGATGGTGCTACCTCTTTCTGGAGACTTCCATATTGGA
_____ >|< ─── exon 3 ─────────
TTCTTACCAATGTACTGCAGAGATAAGTTTAGCTGACCTGGCTACCATATTTTTTGCCCA
TTCTTACCAATGTACTGCAGAGATAAGTTTAGCTGACCTGGCTACCATATTTTTTGCCCA
```

B

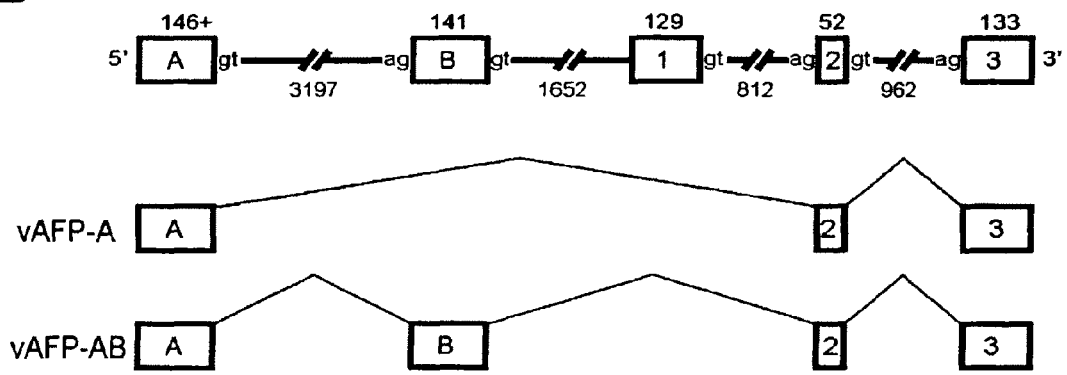

FIGURE 3

```
gcagcaaatgggaaaggtgaagtcttgtactctagagcatgattcaaatagataggctca   60
aattaaacaaatggagggatagtttgttctgcctaaaagcagtaataggagggaatcta  120
gaagctgggtctggatgggaagacattaagaaaggagagggagagagagcaagcaagaag  180
gaggccggtcagggctctacaagaagagagtcaggtggtattgatacgagtggaaaagat  240
cttttatgttttatgcctagttccttgatacaaacttgtggtgggggttcttgaaaaa   300
gtgattggggactatctgatctggggtttagggcagggaagaaacagcatgtaaaggaga  360
aaagacagagcatttgttaaagagaatttaacagcaagaggaaataagaaccaatgatac  420
caaggataaacgcagtccttaactcccctatcactgaattcttagaaatatgggggtagg  480
ggtggtggtggtaattctgttttctccccataggtgagataagcattgggttaaatgtgc  540
tttctctctctccctctccttctaagaattaagggacagactatgggctggaggactt   600
  a a a a a- a a    a          a
tgaggatgtctgtctcataacacttgggttgtatctgttctatggggcttgttttaagct  660
tggcaacttgcaacagggttcactgactttctcccagcccaaggtactgtcctcttttt  720
                                                 a
catatctgttttggggcctctggggcttgaatatctgagaaaatataaacatttcaataa  780
tgttctgtggtgagatgagtatgagagatgtgtcattcatttgtatcaatgaatgaatga  840
```

FIGURE 4

A
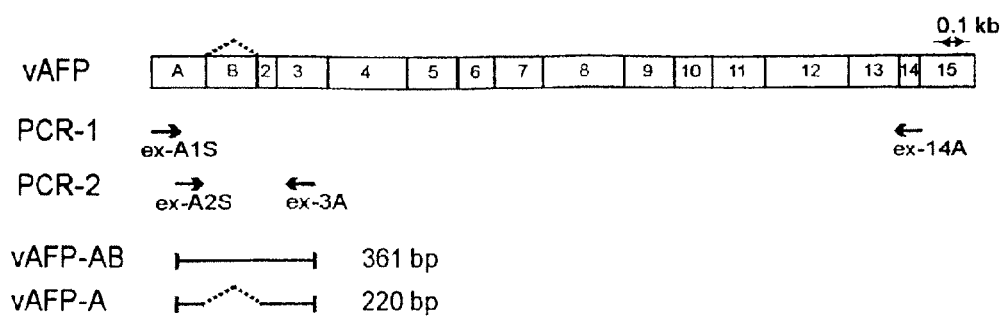
B
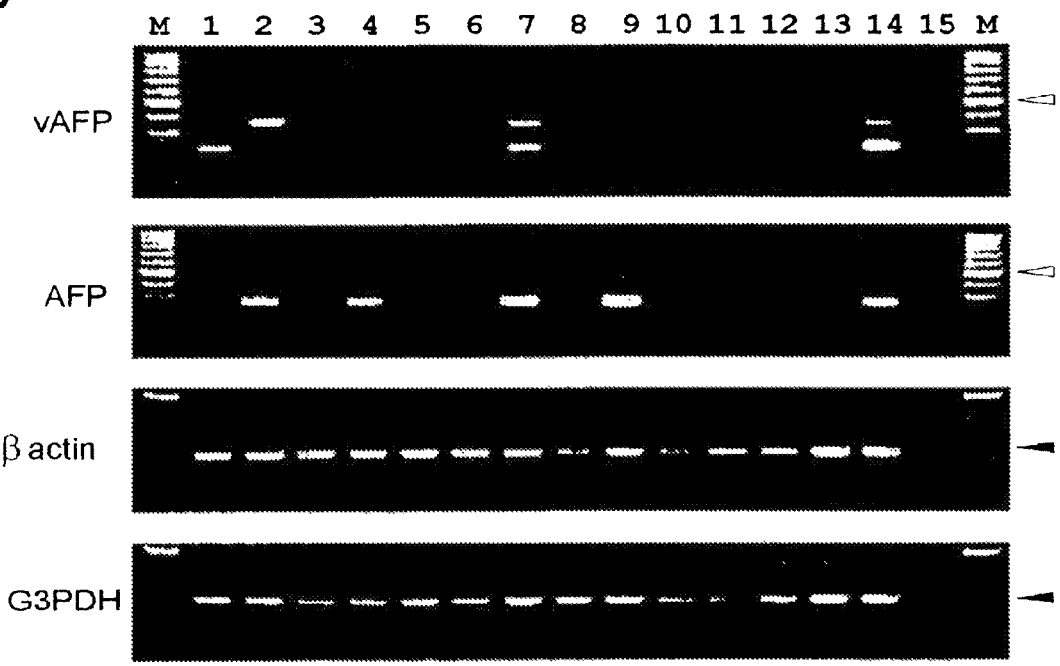
FIGURE 6

A
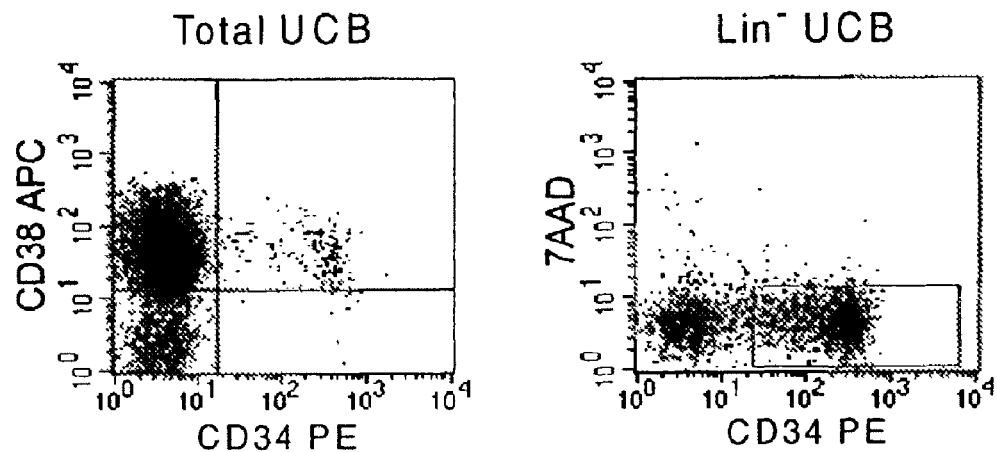
B
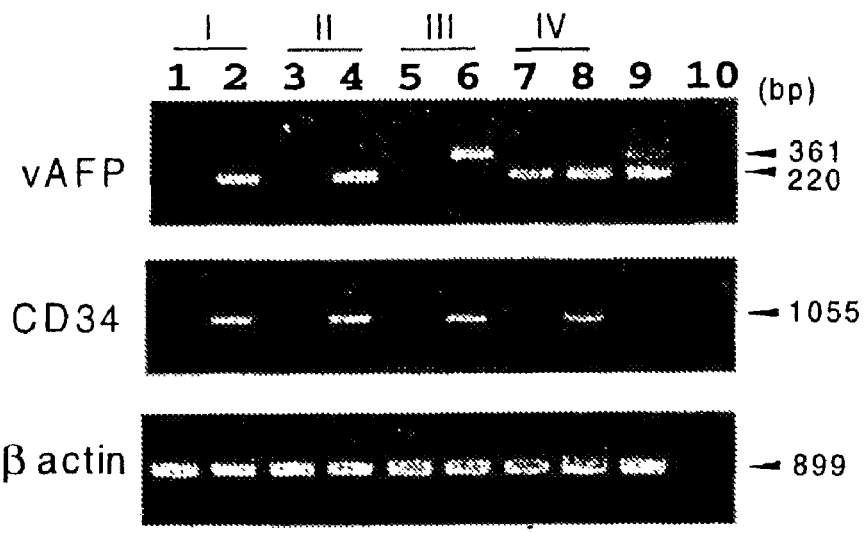
FIGURE 7

VARIANTS OF ALPHA-FETOPROTEIN CODING AND EXPRESSION SEQUENCES

1.0 CROSS REFERENCE TO RELATED APPLICATION DATA

This application is a division of U.S. patent application Ser. No. 10/254,676, filed Sep. 26, 2002, which claims priority to U.S. Provisional Application 60/324,540, filed Sep. 26, 2001, the disclosures of which are hereby incorporated by reference in their entirety.

1.1 Sequence Listing

The instant application contains a Sequence Listing which has been submitted in ASCII format via EFS-Web and is hereby incorporated by reference in its entirety. Said ASCII copy, created on Aug. 9, 2011, is named 69961803.txt and is 25,252 bytes in size.

2.0 FIELD OF THE INVENTION

The present invention relates generally to methods of identifying forms of alpha-fetoprotein unique to hemopoietic progenitors and to hemopoietic cancers and thereby, hemopoietic stem cells or progenitors and cancers related thereto, as a marker for cell cloning and identification of cloned cells, and for evaluating developmental stages in organs and organisms.

3.0 BACKGROUND OF THE INVENTION

Multipotent stem cells, cells capable of extensive growth without losing their potential for differentiating into a plurality of cell types, are found in fetal and various adult tissues. Multipotent stem cells have been isolated from fetal tissue and bone marrow.

Cell differentiation in the developing embryo is regulated by extrinsic inductive signals and an intrinsic programmed genetic code. Differentiation into the three germ layers (ectoderm, endoderm, and mesoderm) from primitive ectoderm (epiblast) is a crucial step during development and previously thought to be an irreversible process leading to a germ layer giving rise to unique types of cells, e.g., epidermal or neuronal cells from ectoderm; epithelial cells in internal organs or digestive tract from endoderm; and hemopoietic and mesenchymal cells from mesoderm. Recent studies of cell transplantation, however, have indicated that somatic stem cells or progenitor cells from adult tissues and with characteristic tissue-specific markers were able, possibly, to generate cells with fates different from those heretofore recognized as descendants of a specific germ layer. Although the evidence for this is still inconclusive, if proven true it would an example of a process called "transdifferentiation" and leads to questions about possible mechanisms. A candidate example of putative transdifferentiation is that of CD45+ hemopoietic stem cells giving rise to mature hepatocytes.

Adult liver parenchymal cells consist of hepatocytes and biliary epithelial cells. They are derived from common precursors, hepatoblasts, that come from foregut endodermal stem cells by an inductive signal(s) from the septum transversum surrounding the outpouching of the endoderm. Although it is not known whether hemopoietic cells can differentiate into hepatoblasts, there does appear to be a sub-population of progenitors in the bone marrow capable of maturing into hepatocytes and sharing critical antigenic markers with that of hemopoietic progenitors; therefore, these hemopoietic progenitor cells should express some endodermal markers before full differentiation into hepatocytes.

Alpha-fetoprotein (AFP) is a major serum protein produced primarily by endoderm-derived yolk sac and by hepatoblasts as well as more differentiated fetal hepatic cells. AFP is one of the earliest markers for endodermal differentiation; the transcriptional expression starts at visceral and definitive endoderm in the early embryo and is regulated tightly in a developmental and tissue-specific manner. Therefore, in most studies in which is assessed endodermal differentiation of human embryonic stem cells or embryonic germ cells, the expression of AFP mRNA has been investigated and used as a marker of endoderm.

4.0 SUMMARY OF THE INVENTION

The inventors have identified at least two variant forms of human AFP transcripts. The variant forms of human AFP transcripts are associated with certain non-hepatic tissues. In particular, the variant forms are associated with a multipotent hemopoietic cell line, K562, and with bone marrow progenitors. The cDNA sequences revealed that the differences in the variant AFP (vAFP) mRNAs compared to that of the authentic transcript, consisting of 15 exons, are the presence of one or two unique exons, named exon A and exon B, replacing exon 1 of AFP. The variant forms were detected in normal CD34$^+$Lin– hemopoietic progenitor cells but not in mature blood cells. The expression of the variant AFP transcripts suggests that hemopoietic progenitors are in an immature state that is permissive to express certain types of transcripts that have been considered unique to endoderm.

Accordingly, one aspect of the invention is an isolated nucleic acid having a polynucleotide sequence corresponding to SEQ ID NO:1, a homolog thereof, or a complement thereof. The nucleic acid can be suitable for detection of a variant form of alpha-fetoprotein mRNA.

One aspect of the invention is a nucleic acid primer in which the primer comprises at least ten contiguous nucleotides in the polynucleotide sequence corresponding to SEQ ID NO:1.

In one aspect, the invention comprises a polypeptide translated from a nucleic acid comprised at least in part by a polynucleotide sequence corresponding to SEQ ID NO:1 or a complement thereof. In one embodiment the polynucleotide sequence is at least 97% homologous to SEQ ID NO:1.

One aspect of the invention is an isolated nucleic acid having a polynucleotide sequence corresponding to SEQ ID NO:2, a homolog thereof, or a complement thereof. In one embodiment the nucleic acid is suitable for detection of a variant form of alpha-fetoprotein mRNA.

In one aspect, the invention is a nucleic acid primer in which the primer comprises at least ten contiguous nucleotides of a polynucleotide sequence corresponding to SEQ ID NO:2.

One aspect of the invention is a polypeptide translated from a nucleic acid comprised at least in part by a polynucleotide sequence corresponding to SEQ ID NO:2. In one embodiment the polynucleotide sequence is at least 97% homologous to SEQ ID NO:2.

In one aspect, the invention is a composition suitable for detection of variant alpha-fetoprotein mRNA comprising: (a) a first nucleic acid primer in which the first primer comprises at least ten contiguous nucleotides of the polynucleotide sequence corresponding to SEQ ID NO:1, and optionally (b) a second nucleic acid primer in which the second primer comprises at least ten contiguous nucleotides of the polynucleotide sequence corresponding to SEQ ID NO:2.

One aspect of the invention is a composition comprising a nucleic acid in which the nucleic acid encodes a polypeptide encoded in all or in part by the nucleic acid of SEQ ID NO:1 or the nucleic acid of SEQ ID NO:2. In another embodiment the invention is a composition comprising an isolated nucleic acid having a polynucleotide sequence corresponding to SEQ ID NO:1, SEQ ID NO:2, or complements thereof.

In one aspect, the invention is a nucleic acid with a sequence spanning the splice from exon A to exon 2, from exon A to exonB, or from exon B to exon 2. Thus, in one aspect, the invention is a composition suitable for detection of a variant form of alpha-fetoprotein, the composition comprising a polynucleotide of sequence N1-C-C-A-A-G-C-T-T-N2 (SEQ ID NO: 67), N1-C-C-A-A-G-G-T-A-N2 (SEQ ID NO: 68), or N1-G-G-A-G-A-C-T-T-N2 (SEQ ID NO: 69), in which each of N1 and N2 have a sequence selected from the group consisting of AA, AC, AG, AT, AX, CA, CC, CG, CT, CX, GA, GC. GG, GT, GX, TA, TC, TG, TT, TX, XA, XC, XG, XT, and XX, in which A, C, G, T, and X represent the 2'-deoxyribonucleic acid moieties of adenine, cytidine, guanine, thymidine, and no nucleic acid, respectively.

One aspect of the invention is a composition suitable for detection of a variant alpha-fetoprotein comprising a polynucleotide of sequence N1-N2-N3-N4-N5-N6-N7-N8-N8-N10, in which each of N1, N2, N3, N4, N5, N6, N7, N8, N9, and N10 are independently A, C, G, T, or no nucleotide moiety, with the proviso that no more than one nucleotide can vary from the sequence C-C-C-A-A-G-C-T-T-C (SEQ ID NO: 70), C-C-C-A-A-G-G-T-A-T (SEQ ID NO: 71), or T-G-G-A-G-A-C-T-T-C (SEQ ID NO: 72). In this embodiment, the length of the polynucleotide can be from nine to 25 bases, for example ten, or twelve.

In one aspect, the invention is a polynucleotide primer comprising: seven or more nucleotide residues capable of hybridizing under stringent hybridization conditions to a nucleic acid encoding a variant form of alpha-fetoprotein. In one embodiment the nucleic acid is not capable of hybridizing to a second nucleic acid encoding normal, hepatic-specific alpha-fetoprotein.

The stringent hybridization conditions comprise any conditions considered stringent in the art of the invention. In one embodiment stringent hybridization conditions comprise 3× to 8×SSC. In another embodiment the hybridization conditions comprise 6×SSC, 0.5% SDS at 65° C., and washing at 2×SSC at room temperature. In another embodiment the hybridization conditions are 7% (w/v) sodium dodecylsulfate, 0.5M NaPO$_4$, pH 7.0, 1 mm EDTA, at 50° C.; followed by washing with 1% sodium dodecylsulfate.

In one aspect, hybridization is carried out at 55-65° C. under conditions of 6×SSC, 0.5% SDS, and washing at 2×SSC at room temperature.

One aspect of the invention is a method of detecting a variant alpha-fetoprotein mRNA comprising: (a) combining a sample suspected of containing a variant form of alpha-fetoprotein, at least one primer capable of hybridizing to a variant form of AFP mRNA, and reagents for PCR to form a mixture, (b) subjecting the mixture to thermocycling, and (c) determining the absence or presence of cDNA corresponding to a variant form of AFP mRNA. In one embodiment the primer comprises at least ten continuous nucleotides of a polynucleotide sequence corresponding to SEQ ID NO:1, SEQ ID NO:2, or complements thereof. In one embodiment the mixture comprises a first primer comprising at least ten contiguous nucleotides corresponding to SEQ ID NO:1 or a complement thereof and a second primer comprising at least ten contiguous nucleotides of a polynucleotide sequence corresponding to SEQ ID NO:2 or a complement thereof. In another embodiment the mixture comprises a first primer comprising at least ten contiguous nucleotides corresponding to SEQ ID NO:1, SEQ ID NO:2, or complements thereof and a second primer, comprising at least ten contiguous nucleotides of a polynucleotide sequence corresponding to mammalian AFP, or a complement thereof. In one embodiment the primers can be between about 15 and about 25 nucleotides in length.

One aspect of the invention is a method of identifying or detecting hemopoietic stem or progenitor cells comprising determining the presence or absence of a variant form of alpha-fetoprotein mRNA in cells suspected of being hemopoietic stem or progenitor cells.

In one aspect, the invention is an isolated nucleic acid encoding a variant form of alpha-fetoprotein (AFP) preferentially expressed in progenitor cells, in which exon 1 of exons 1-14 of alpha-fetoprotein has been replaced by a polynucleotide sequence corresponding to SEQ ID NO:1, SEQ ID NO:2, or a fusion thereof.

One aspect of the invention is a probe capable of detecting the expression of a variant form of alpha-fetoprotein (AFP) comprising a nucleic acid consisting essentially of at least 10 contiguous nucleotides of the polynucleotide sequence corresponding to SEQ ID NO:1, a homolog thereof, or a complement thereof.

In one aspect, the invention is a recombinant expression vector comprising the isolated nucleic acid of SEQ ID NO:1, SEQ ID NO:2, or both.

One aspect of the invention is a method for detecting a polynucleotide, which encodes a variant form of AFP, in a sample comprising: (a) hybridizing the nucleic acid corresponding to either SEQ ID NO:1 or a portion thereof having 10 or more nucleotides, to a nucleic acid present in a sample to be tested to form a hybridization complex; and (b) detecting the hybridization complex, if any. The presence of the hybridization complex can indicate the presence of a polynucleotide encoding a variant form of AFP in the sample. Moreover, the conditions for hybridization can be stringent.

In one aspect, the invention is a method of preparing a subpopulation of cells enriched in hemopoietic progenitors comprising: (a) providing a cell suspension comprising subpopulations of various types of cells and (b) selecting a subpopulation of cells which expresses a variant form of alpha-fetoprotein nucleic acid to provide an enriched population of hemopoietic progenitors is provided. In another aspect, the invention is a composition comprising cells capable of expressing vAFP, at least a portion of which cells are hemopoietic progenitors, or their progeny. The cells, or at least a subpopulation thereof, can be from bone marrow. In one aspect, the invention is a composition comprising at least one subpopulation of cells which comprises hemopoietic progenitors, or their progeny, capable of expressing variant AFP. The variant AFP can include exon A, exon B, combinations thereof, or variants thereof. The subpopulation of the composition can optionally be derived from bone marrow.

One aspect of the invention is a method of identifying a tumor comprising:
(a) providing a tumor or a tissue sample suspected of including tumor tissue and
(b) detecting the absence or presence of variant alpha-fetoprotein nucleic acid whereby a tumor is identified.

In one aspect, the invention is a method of identifying a hemopoietic progenitor comprising: (a) providing a putative progenitor and (b) detecting a variant alpha-fetoprotein nucleic acid whereby a hemopoietic progenitor is identified.

One aspect of the invention is a method of identifying a hepatopoietic progenitor comprising: (a) providing a putative progenitor and (b) measuring a substantial absence of variant alpha-fetoprotein nucleic acid whereby a hepatopoietic progenitor is identified.

One aspect of the invention is a polypeptide having an amino acid sequence corresponding to SEQ ID NO:17 or an analog thereof. One embodiment of the invention is an antibody against a polypeptide having an amino acid sequence corresponding to SEQ ID NO:17, or an analog thereof, or a fragment thereof. In one embodiment the fragment is at least about three amino acids and in another embodiment the fragment is at least about four amino acids.

5.0 BRIEF DESCRIPTION OF THE FIGURES

FIG. 1 panel A depicts the exon structure of the AFP genome and panel B depicts the splicing of exons to form AFP mRNA.

FIG. 2 panel A illustrates sizing gel electropherograms of mRNA exons identified by rt-PCR and panel B illustrates the identification of exons used in AFP transcripts.

FIG. 3 panel A depicts the nucleotide sequences (SEQ ID NOS 37, 39, and 38 respectively, in order of appearance) of exons A, B, 2, and 3 and panel B depicts the splicing of mRNA exon transcription products to form normal AFP (top), variant AFP-A (middle), and variant AFP-B (bottom).

FIG. 4 depicts the genomic sequence of variant AFP exon A (SEQ ID NO: 40).

FIG. 6 depicts selective expression of variant AFP transcripts in normal human tissues. Panel A depicts the splicing of exons to form the mRNA of two variants of AFP, and panel B depicts sizing gel electrophereograms of rt-PCT of variant AFP (top), normal AFP (second from top), beta actin (third from top), and glycerol-3-phosphate dehydrogenase (bottom).

Figure 2:
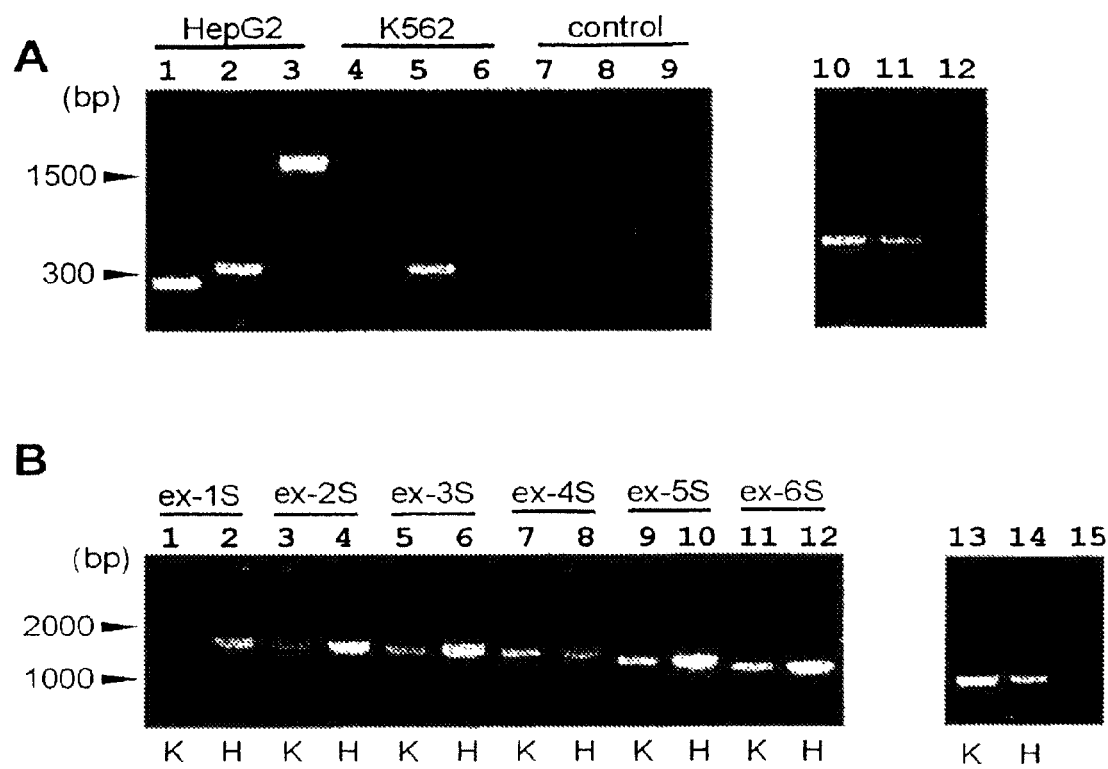

FIG. 7 panel A depicts a two color FACS sort and panel B depicts sizing gel electropherograms of variant AFP, CD34, and beta-actin.

6.0 DETAILED DESCRIPTION OF THE INVENTION

In one aspect, the invention is a method of assay for a variant alpha-fetoprotein mRNA comprising: (a) combining a sample, a first primer, a second primer, and reagents for PCR to form a mixture, (b) subjecting the mixture to thermocycling, and (c) identifying the absence or presence of variant AFP cDNA, in which the first primer, the second primer, or both are capable of hybridizing to the variant alpha-fetoprotein mRNA. This method can be one in which the first primer comprises at least ten contiguous nucleotides according to the DNA of SEQ ID NO:1 or a complement thereof. In one aspect, this method can be one in which the second primer comprises at least ten contiguous nucleotides according to the DNA of SEQ ID NO:2 or a complement thereof. In another alternative, the second primer comprises at least ten contiguous nucleotides according the DNA sequence of a mammalian AFP, or a complement thereof. In one embodiment the mammal is human.

One aspect of the invention is a method of identifying or detecting hemopoietic stem or progenitor cells comprising determining the presence or absence of a variant form of alpha-fetoprotein mRNA in cells or a sample from cells, suspected of being hemopoietic stem or progenitor cells. This method can be one in which the determining step comprises PCR using one or more primers to one or more variant forms of alpha-fetoprotein. This method can also be one in which the determining step comprises immunodetection, for example using antibody to at least a part of the variant alpha-fetoprotein. The immunodetection can be any method standard in the art, including ELISA, RIA, immunohisto chemistry and, immunofluorescence. The antibody can be directed to any epitope of a variant form of AFP.

In one aspect, the invention is an isolated nucleic acid encoding a variant form of AFP preferentially expressed in progenitor cells, in which exon 1 of exons 1-14 of AFP has been replaced by a polynucleotide sequence corresponding to SEQ ID NO:1, SEQ ID NO:2 or a fusion thereof. In one embodiment, the nucleic acid includes at least 100 contiguous nucleic acid residues corresponding to the N-terminal half of a variant form of AFP. In another embodiment, the nucleic acid includes at least 50 contiguous nucleic acid residues corresponding to the N-terminal half of a variant form of AFP.

One aspect of the invention is a probe for detection, measurement, or both, of a AFP variant gene expression, which comprises any one of (a) a purified, isolated or synthesized DNA consisting of a sequence of at least 10 contiguous nucleotides in the DNA of SEQ ID NO:1, (b) a purified, isolated or synthesized DNA complementary and identical in length to DNA (a), or (c) a purified, isolated or synthesized DNA having at least 90% homology to DNA (a) or (b); or a polynucleotide sequence which is complementary thereto. In one embodiment the homology is about 99%. The probe can be of any length standard in the art without limiting to a specific length, the probe can be 100 to 300 nucleotides in length. The probe can be about 150 to about 250 nucleotides in length.

One aspect of the invention is a method for detecting a polynucleotide which encodes a variant form of AFP in a sample comprising: (a) hybridizing the nucleic acid corresponding to either SEQ ID NO:1 or SEQ ID NO:2, or a portion thereof having 10 or more nucleotides, to a nucleic acid in the sample to be tested to, form a hybridization complex; and (b) detecting the hybridization complex, if any. The presence of the hybridization complex indicates the presence of a polynucleotide encoding variant AFP in the sample. In this method the nucleic acid can be amplified by the polymerase chain reaction prior to hybridization.

Stringent hybridization conditions are those known in the art that permit hybridization of only closely homologous polynucleotides. The stringent conditions can include a hybridization medium having 6×SSC, 0.5% SDS, used at a temperature of 65° C. or any other medium and condition known in that art as a stringent condition. Hybridization can be followed by washing in 2×SSC at room temperature.

The invention can be illustrated further by the figures provided.

FIG. 1 is a schematic representation of the human AFP gene, the AFP transcript, and the position of primers used for RT-PCR. Panel A illustrates that the Human AFP gene consists of 15 exons and 14 introns and spans approximately 20,000 base pairs. Part B illustrates the location of the initiation methionine codon (ATG) and the termination codon (TAA) of a AFP transcript in exon 1 and exon 14, respectively. The approximate positions of sense primers and anti-sense primers are shown.

FIG. 2 depicts the expression of a variant form of AFP mRNA in the cell line K562, a hematopoietic cell line. In panel A, the expression of AFP mRNAs in K562, and hepatocellular carcinoma cell line, HepG2, are analyzed by RT-PCR using three different primer combinations. Primer combinations of ex-1S and ex-3A, ex-12S and ex-14A, and ex-1S and ex-14A are used to amplify exon 1 to exon 3 (lane 1, 4, and 7), exon 12 to exon 14 (lane 2, 5, and 8), and exon 1 to exon 14 (lane 3, 6, and 9), respectively. Control reaction is performed without a template. The C-terminus part of AFP transcript is expressed in K562. Panel B depicts the identification of exons used in a AFP transcript from K562. RT-PCR of primer combinations of a series of 5' primers from exon 1 to exon 6 (ex-1S to ex-6S) and ex-14A as the 3' primer are performed with cDNA from K562 (lane K) and HepG2 (lane H). HepG2 cDNA is diluted at one to one hundred times. K562 expresses the entire coding exons, except for exon 1, in the authentic AFP transcript. The right sections of panels A and B show expression of beta-actin (A: lane 10 HepG2; lane 11, K562; lane 12, control and B: lane 15, control). The open arrow heads indicate 1 k bp.

FIG. 3 depicts sequences and the genomic structure of two variant forms of AFP expressed in K562. Panel A depicts DNA sequences of two variant forms of AFP transcripts isolated from K562 cDNA. Panel B is a schematic illustration of the genomic structure of a variant form of AFP. Open boxes and horizontal lines indicate exons and introns, respectively. Their lengths in nucleotides are indicated by numbers above and below these elements. One type of the variant forms used one additional exon (exon A) located at approximately 5 kb upstream from exon 1. The other type used exon A and another exon (exon B) located at approximately 1.6 kb from exon 1. The genomic organization of the variant forms was deduced from the genomic sequence of the AFP gene.

FIG. 4 depicts the genomic sequence of a variant form of AFP exon A. The nucleotide sequence in the open box indicates exon A cloned by anchored PCR. The nucleotide position from the top left is indicated on the right. The sequence between 517 to 739 is confirmed as present in K562, HepG2, and MRC5. Open circles mark nucleotides which differ from those in a previous report in which the nucleotides indicated underneath. Facing arrows and a double underline indicate an inverted repeat and putative TATA box, respectively. Possible binding sites of transcriptional factors GATA-X (closed circles), MZF-1 (open squares), AML-1 (closed squares), and NF-Y (closed triangles) are shown above nucleotides. Binding motifs are analyzed by TRANSFAC.

Figure 5:
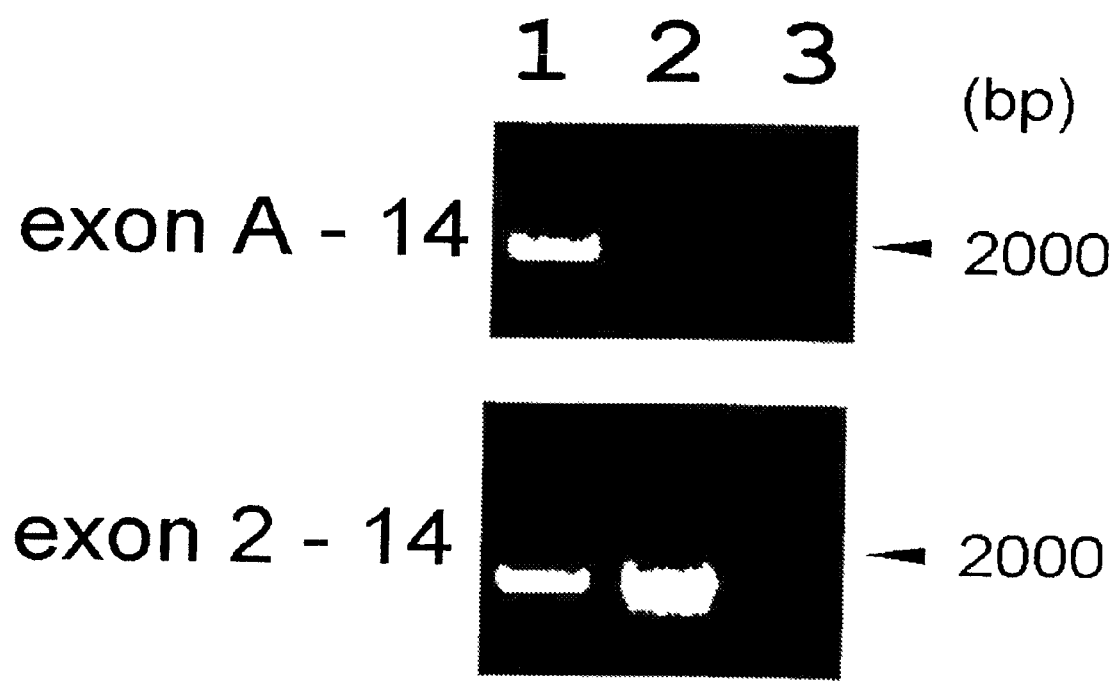
FIG. 5 depicts selective expression of variant forms of AFP in K562 cells.

FIG. 5 depicts selective expression of variant AFP transcripts in K562. RT-PCR of the primer combination of exon A primer (ex-AS) and ex-14A primer is performed with cDNA from K562 (lane 1) and HepG2 (lane 2). K562, but not HepG2, expresses a variant form of an AFP transcript. Note the strong signal of HepG2 by RT-PCR using ex-2S and ex-14A. This indicates that HepG2 expresses the authentic form only. Equal amounts of cDNA are used for the reaction. Lane 3 is a control reaction.

FIG. 6 depicts RT-PCR analyses of variant forms of AFP transcripts in normal human tissues. Panel A depicts a nested PCR strategy. A first PCR (PCR-1) of the primer combination of ex-A1S/ex-14A and a second PCR (PCR-2) of that of ex-A2/ex-3A are illustrated. The amplified DNA fragments of two AFP variant forms are distinguishable in agarose electrophoresis. Panel B depicts analysis of the expression of variant AFP mRNAs in cDNAs from various human tissues: lane 1, bone marrow; lane 2, thymus; lane 3, spleen; lane 4; small intestine; lane 5, colon; lane 6, stomach; lane 7, brain; lane 8, heart; lane 9, kidney; lane 10, liver; lane 11, lung; lane 12, trachea; lane 13, MRC5; lane 14, K562; and lane 15, no template. Nested RT-PCR of authentic AFP transcript is performed in the same human tissues cDNA. The results of single step RT-PCR of beta actin and G3PDH are shown. Expression of variant AFP mRNAs is detected in bone marrow, thymus, and brain. Open and closed arrowheads indicate 500 bp of 100 bp ladder and 1000 bp of 1000 bp ladder marker, respectively.

FIG. 7 depicts expression of variant forms of AFP transcripts in normal human hematopoietic progenitors. Panel A depicts representative dot plots of flow cytometric analysis for CD34 and CD38 expression in umbilical cord blood cells after ficoll centrifugation (left). The CD34+ cell population on the average is 2.3% of the whole. The CD34+ cell population is enriched after removing Lin+ cells (right). The live CD34 cell fraction (inside of open box) is sorted for RT-PCR analysis. Panel B depicts RT-PCR analysis of variant forms of AFP transcripts in sorted umbilical cord blood cells. Roman numerals indicate individual UCB samples. RNAs are isolated from unfractionated (lane 1, 3, 5, and 7) or CD34+Lin− UCB cells (lane 2, 4, 6, and 8), and nested PCR is performed as described in FIG. 5A. CD34+Lin− cells in UCB expressed variant forms of AFP. Lane 9 is K562 cells and lane 10 is a control reaction.

7.0. EXAMPLES

The following examples are illustrative of specific uses of the invention, but the claimed invention is not limited by the specific examples provided.

7.1. Variant AFP mRNA Expressed in K562, a Human Erythroleukemia Cell Line

The human AFP gene consists of 15 exons, in which the coding sequence is from exon 1 to exon 14 (FIG. 1A). Two different portions of the AFP cDNA sequence are selected as target sequences of RT-PCR. The primer combination of ex-1S and ex-3A is for the amplification of exon 1 containing the initiation methionine to exon 3, whereas that of ex-12S and ex-14A amplifies exon 12 to exon 14 containing the termination codon (FIG. 1B). The results of the PCR amplification are shown in FIG. 2A. Both combinations of primers resulted in amplification bands which are strongly detected in the RNA from HepG2, a hepatocellular carcinoma cell line. By contrast, only the specific band of the C-terminal portion is detected by the primer set of ex-12S and ex-14A in the RNA from K562, an erythroleukemia cell line. These results might suggest that K562 expresses a short form of the authentic AFP (authentic AFP) transcript without the N-terminus. In fact, the result of the PCR for the whole coding region of AFP using ex-1S and ex-14A primers shows that the single remarkable band of 1.8 Kb (lane 3) is amplified from the HepG2 cDNA, whereas there is no band in K562 (lane 6).

Only one AFP gene per haploid genome has been demonstrated in rats, mice, and humans. In all three species, the AFP genes are organized similarly into 15 coding exons interrupted by 14 introns. Although there is no report about any variant form of the AFP mRNA in humans, several short forms of the AFP transcript have been characterized in rat. All those transcripts share a common 3' sequence. Detailed analysis of one variant form of them showed that the rat vAFP lacks the first seven exons of authentic AFP mRNA. Thus, the inventors designed new sense primers for exon 7 and exon 8 to see whether the variant form of human AFP mRNA in K562 is similar to those of rat, because a designated V exon located in the seventh intron of the rat gene has been identified as the first exon of the variant forms. By RT-PCR analysis, the primer for exon 7, as well as one for exon 8, detected vAFP in K562. Thus, the human vAFP transcript is not similar to that in the rat. Therefore, a series of 5' primers from exon 2 to exon 6 are constructed (FIG. 1) to detect the difference between authentic and variant forms of AFP transcripts. Surprisingly, the entire coding exons, except for exon 1, are shared in the variant form of AFP in K562 (FIG. 2b).

7.2. Molecular Cloning of Variant AFP cDNA from K562

To identify the structure of the N-terminus portion of the vAFP transcript in K562, anchored PCR is performed by standard methods. As a result, two types of variant transcripts are identified, as shown in FIG. 3A. Comparing the sequences of the variant transcripts to the Genbank database, two regions of genomic sequence of human AFP gene are identified. One type of the variant forms uses an additional exon, designated exon A, located at 5 kb upstream from exon 1 (FIG. 3B). The other type used exon A and another exon, designated exon B, located at 1.6 kb from exon 1 (FIG. 3B). Among 19 clones analyzed, 15 clones are type-A; 3 clones are type-AB; and one clone is the germ line transcript of intron 1. Although the genomic sequences of AFP region were reported from a couple of sources, some nucleotides in the exon A of K562 differ from the reported genomic sequence by one nucleotide base. Therefore, the K562 genomic sequence of exon A is compared to the cloned cDNA sequence to determine whether the difference results from artifacts of the anchored PCR. While the variant cDNA and genomic DNA of K562 are identical, a TC-rich sequence at the right upstream of the variant transcripts in K562 is substituted to produce the AC-rich sequence in the previous report. Thus, the genomic sequence of normal human fibroblasts as well as HepG2 is compared to that of K562 to see whether the mutation is K562-specific or not. However, no differences in all three genomic sequences of the exon A region of K562 are observed. In FIG. 4 is shown the overall genomic sequence in the region of exon A from our data combined with the Genbank database. As shown in the figure, possible binding sites of several transcriptional factors such as GATA-X, MZF-1, and AML-1, with functions crucially associated with early hematopoiesis, can be identified around exon A. Also, a possible TATA box, albeit not a typical one, is indicated. In addition, an inverted repeat of 30 nucleotides, including the TC-repeat sequence with the 180 bp interval, is identified (FIG. 4).

7.3. Selective Expression of Variant Transcripts in K562

The expression pattern of the variant and authentic transcripts of AFP is studied in K562 and HepG2. A sense primer of exon A for RT-PCR is designed. The combination of the exon A primer and exon 14 primer, ex-14A, successfully detects the transcripts in K562, but not HepG2. The detected bands in K562 are cloned and sequenced to confirm the amplified products. As expected, DNA sequencing shows that the two types of variant AFP transcripts uses exon A and B or exon A only and are followed by exon 2 to exon 14. The number of clones with a type A sequence is 7 out of 12, while that of the type AB clone is 5 out of 12. This suggests that two types of vAFP are expressed equally in K562. The far stronger signal of HepG2 by RT-PCR using ex-2S and ex-14A indicates that HepG2 is expressed the authentic form only. This result clearly demonstrates that the pattern of expression of variant or authentic forms of AFP in K562 is opposite to that of HepG2.

7.4. Expression of Variant Forms of AFP in Normal Human Tissues

Variant transcripts of AFP expressed in normal cells are assessed by nested (two step) RT-PCR to detect the very low level expression. The first PCR is performed with primers, ex-A1S and ex-14A, to amplify whole the coding sequence of variant forms. Subsequently, nested PCR is carried out by an internal primer combination, ex-A2S and ex-3A. This nested PCR can distinguish type A and type AB by the molecular size (FIG. 5A). The results of PCR show that the tissue distribution of the variant AFP transcripts is fairly restricted. Only brain and primary hemopoietic organs, such as bone marrow and thymus, express the transcripts. Other tissues, including liver, lung, trachea, kidney, stomach, small intestine, colon, heart and spleen, do not have cells expressing vAFP. On the other hand, authentic AFP is detected in brain, kidney, small intestine, and thymus, but not in bone marrow. The pattern corresponds with that of embryonic expression of authentic AFP. These results strongly suggest that hemopoietic progenitors, but not differentiated cells, express vAFP, since spleen is a secondary hemopoietic organ, in which hemato-lymphopoiesis does not normally occur. In addition, cDNA from peripheral blood cells does not show the expression of vAFP. The lack of expression in normal human fetal fibroblasts (FIG. 6B, lane 13) and small intestine (FIG. 6B, lane 4) suggests that the vAFP expression is not associated simply with the status of cell proliferation.

7.5. Variant Transcripts of AFP Expressed in Hemopoietic Progenitors

The RT-PCR of tissue RNAs cannot define which cells express the variant forms of AFP transcripts, because tissues are comprised of many cell types. Bone marrow and thymus, for example, consist of very heterogeneous cell populations. Therefore, purified hemopoietic progenitors from umbilical cord blood are evaluated by flow cytometric sorting to learn whether or not they express vAFP. CD34+CD38-Lin– cells are a negligible subpopulation in unfractionated umbilical cord blood (FIG. 6A) but consist of pure hemopoietic progenitors and include hemopoietic stem cells. The CD34+ CD38-cells are highly enriched after removing Lin-positive cells (FIG. 6A). Both unfractionated live cells (7AAD-) and CD34+Lin– cells are isolated by flow cytometric sorting, and the RNAs extracted are subjected to nested PCR for vAFP. A total of four different cord blood samples are tested. As shown in FIG. 6B, the expression of vAFP transcripts are detected successfully in all samples of enriched hemopoietic progenitors (lanes 2, 4, 6, and 8), but generally not in whole cord blood cells (lanes 1, 3, and 5), although observed in sample 7. The amplified bands are exactly identical DNA sequences to those of type A and type AB from K562 (FIG. 3A) by cloning and DNA sequencing. Similarly, cells are isolated from other tissues, for example bone marrow, and evaluated for expression of vAFP before and after optional cell sorting for surface markers, for example CD45, the Lin markers, or both.

7.6. A Homolog of vAFP: $G^{10}T^{20}$-variantA-$AFP^{97}$

A homolog of a variant AFP, designated $G^{10}T^{20}$-variant A-$AFP^{197}$, and described as SEQ ID NO:3, varies from variant A-AFP by single point substitutions at two loci. The $G^{10}T^{20}$-variant A-$AFP^{197}$ and complements thereof and portions thereof can be used for identification of variant AFP in cells—particularly in stem and progenitor cells from bone marrow and other hemopoietic organs, for cell cloning and identification of cloned cells, for tumor identification, for evaluating developmental stages in organs and organisms, and as a hybridization marker for exon 1 or variants of exon 1. Other homologs of varA-AFP with about 99% homology are also useful for these purposes.

7.7. A Homolog of vAFP: $A^{30}C^{90}$-variantA-$AFP^{197}$

A homolog of variant AFP, designated $A^{30}C^{90}$-variant A-$AFP^{197}$, and described as SEQ ID NO:4, varies from variant A-AFP by single point substitutions at two loci. The $A^{30}C^{90}$-variant A-$AFP^{197}$ and complements thereof and portions thereof can be used for all the purposes that variantA-AFP can be used. Among suitable uses for $A^{30}C^{90}$-variant A-$AFP^{197}$ can be (a) identification of variant AFP in cell isolation—particularly in isolation of stem and progenitor cells from bone marrow and other hemopoietic organs, (b) cell cloning and identification of cloned cells, (c) tumor identification, (d) evaluation of developmental stages in organs and organisms, and (e) as a hybridization marker for exon 1 or variants of exon 1. Other homologs of varA-AFP with about 99% homology are also useful for these purposes.

7.8. A Homolog of vAFP: variantA-(des-T$^{71}$)(des-A$^{152}$)AFP$^{195}$

A homolog of variant AFP, designated variant A-(des-T$^7$)(des-A$^{152}$)AFP$^{195}$, and described as SEQ ID NO:5, varies from variant A-AFP by two nucleotide deletions. The variant A-(des-T$^{71}$)(des-A$^{152}$) AFP$^{195}$ and complements thereof and portions thereof can be used for identification of variant AFP in cell isolation—particularly in isolation of stem and progenitor cells from bone marrow and other hemopoietic organs, for cell cloning and identification of cloned cells, for tumor identification, for evaluating developmental stages in organs and organisms, and as a hybridization marker for exon 1 or variants of exon 1. Other homologs of varA-AFP with about 99% homology and having nucleotide deletions are also useful for these purposes.

7.9. A Homolog of vAFP with Nucleotide Base Insertions

A homolog of variant AFP, characterized by insertion of T into position 78 and C into position 123 and having a total length of 199 bases, and described as SEQ ID NO:6, varies from variant A-AFP by two nucleotide insertions. This form of variant A-AFP$^{199}$ and complements thereof and portions thereof can be used for identification of variant AFP in cell isolation—particularly in isolation of stem and progenitor cells from bone marrow and other hemopoietic organs, for cell cloning and identification of cloned cells, for tumor identification, for evaluating developmental stages in organs and organisms, and as a hybridization marker for exon 1 or variants of exon 1. Other homologs of varA-AFP with about 99% homology and having insertions are also useful for these purposes.

7.10. A Homolog of vAFP: A$^{30}$T$^{55}$C$^{90}$G$^{107}$T$^{124}$I$^{137}$-Variant A-AFP$^{197}$ A homolog of variant AFP, designated A$^{30}$T$^{55}$C$^{90}$G$^{107}$T$^{124}$T$^{137}$-variant A-AFP$^{197}$, and described as SEQ ID NO:7, varies from variant A-AFP by single point substitutions at six loci. The variant A-AFP and complements thereof and portions thereof can be used for identification of variant AFP in cell isolation—particularly in isolation of stem and progenitor cells from bone marrow and other hemopoietic organs, for cell cloning and identification of cloned cells, for tumor identification, for evaluating developmental states in organs and organisms, and as a hybridization marker for exon 1 or variants of exon 1. Other homologs of varA-AFP with about 97% homology are also useful for these purposes.

7.11. Homologs of vAFP with about 90% Homology and about 80% Homology

Homologs of variant AFP, characterized by substitution of nucleotide bases such as to have about 90% homology and about 80% homology are designated SEQ ID NO:8 and SEQ ID NO:9, respectively. These forms of variant A-AFP$^{199}$ and complements thereof and portions thereof can be used for identification of variant AFP in cell isolation—particularly in isolation of stem and progenitor cells from bone marrow and other hemopoietic organs, for cell cloning and identification of cloned cells, for tumor identification, for evaluating developmental stages in organs and organisms, and as a hybridization marker for exon 1 or variants of exon 1. Other homologs of varA-AFP with about 90% and about 80% homology are also useful for these purposes.

7.12. A Homolog of variantB-AFP: C$^{70}$C$^{130}$A$^{189}$-variantB-AFP$^{317}$ A homolog of variant AFP, designated C$^{70}$C$^{130}$A$^{189}$-variantB-AFP$^{317}$, and described as SEQ ID NO:10, varies from variant B-AFP by single point substitutions at three loci. The homolog and complements thereof and portions thereof can be used for identification of variant AFP in cell isolation—particularly in isolation of stem and progenitor cells from bone marrow and other hemopoietic organs, for cell cloning and identification of cloned cells, for tumor identification, for evaluating developmental stages in organs and organisms, and as a hybridization marker for exon 1 or variants of exon 1. Other homologs of variantB-AFP with about 99% homology are also useful for these purposes.

7.13. A Homolog of variantB-AFP: A$^{51}$C$^{179}$T$^{231}$-variantB-AFP$^{317}$ A homolog of variant AFP, designated A$^{51}$C$^{179}$T$^{231}$-variantB-AFP$^{317}$, and described as SEQ ID NO:11, varies from variantB-AFP by single point substitutions at three loci. The homolog and complements thereof and portions thereof can be used for all the purposes that variantB-AFP can be used. Among suitable uses for the homolog can be (a) identification of variant AFP in cell isolation—particularly in isolation of stem and progenitor cells from bone marrow and other hemopoietic organs, (b) cell cloning and identification of cloned cells, (c) tumor identification, (d) evaluation of developmental stages in organs and organisms, and (e) as a hybridization marker for exon 1 or variants of exon 1. Other homologs of variantB-AFP with about 99% homology are also useful for these purposes.

7.14. A Homolog of variantAFP: variantB-(des-C$^{140}$(des-G$^{183}$)(des-C$^{226}$)AFP$^{314}$ A homolog of variant AFP, designated variant B-(des-C$^{140}$)(des-G$^{183}$)(des-C$^{226}$) AFP$^{314}$ and described as SEQ ID NO:12, varies from variant B-AFP by three nucleotide deletions. The homolog and complements thereof and portions thereof can be used for identification of variant AFP in cell isolation—particularly in isolation of stem and progenitor cells from bone marrow and other hemopoietic organs, for cell cloning and identification of cloned cells, for tumor identification, for evaluating developmental stages in organs and organisms, and as a hybridization marker for exon 1 or variants of exon 1. Other homologs of variantB-AFP with about 99% homology are also useful for these purposes.

7.15. A Homolog of variantB-AFP with Nucleotide Base Insertions

A homolog of variant B AFP, characterized by insertion of A into position 60, C into position 120, and T into position 295 and having a total length of 320 bases, and described as SEQ ID NO:13, varies from variant B-AFP by three nucleotide insertions. This form of variant B-AFP$^{300}$ and complements thereof and portions thereof can be used for identification of variant ASP in cell isolation—particularly in isolation of stem and progenitor cells from bone marrow and other hemopoietic organs, for cell cloning and identification of cloned cells, for tumor identification, for evaluating developmental stages in organs and organisms, and as a hybridization marker for exon 1 or variants of exon 1. Other homologs of variantB-AFP with about 99% homology are also useful for these purposes.

7.16. A Homolog of variantB-AFP: A$^{51}$A$^{67}$C$^{75}$T$^{84}$G$^{138}$C$^{179}$T$^{231}$G$^{289}$C$^{292}$-variantB AFP$^{317}$ A homolog of variant AFP, designated A$^{51}$A$^{67}$C$^{75}$T$^{84}$G$^{138}$C$^{179}$T$^{231}$G$^{289}$C$^{292}$-variantB-AFP$^{317}$ and described as SEQ ID NO:14, varies from variantB-AFP by single point substitutions at nine loci. The homolog and complements thereof and portions thereof can be used for all purposes that variantB-AFP can be used. Among suitable luses for the homolog can be (a) identification of variant AFP in cell isolation—particularly in isolation of stem and progenitor cells from bone marrow and other hemopoietic organs, (b) cell cloning and identification of coned cells, (c)

tumor identification, (d) evaluation of developmental stages in organs and organisms, and (e) as a hybridization marker for exon 1 or variants of exon 1. Other homologs of variantB-AFP with about 97% homology are also useful for the purposes.

7.17. Homologs of variantB-AFP with about 90% Homology and about 80% Homology

Homologs of variant AFP, characterized by substitution of nucleotide bases such as to have about 90% homology and about 80% homology are designated SEQ ID NO:15 and SEQ ID NO:16, respectively. These forms of variant B-AFP$^{300}$ and complements thereof and portions thereof can be used for identification of variant AFP in cell isolation—particularly in isolation of stem and progenitor cells from bone marrow and other hemopoietic organs, for cell cloning and identification of cloned cells, for tumor identification, for evaluating developmental stages in organs and organisms, and as a hybridization marker for exon 1 or variants of exon 1. Other homologs of variantB-AFP with about 90% or 80% homology are also useful for these purposes.

7.18. Fluorescence In Situ Hybridization Using Propidium Iodide Counterstaining For Detection of Expression of vAFP mRNA The present invention also encompasses in situ PCR and in situ RT-PCR for detection of DNA and RNA related to normal and variant forms of AFP. The techniques are preferred when the copy number of a target nucleic acid is very low, or when different forms of nucleic acids must be distinguished. The methods are especially important in detecting and differentiating precancer and cancer cells from normal cells. The methods are also useful in detecting subsets of cells destined to become cancer cells. Confirmation of in situ PCR product identity is accomplished by in situ hybridization with a nested $^{32}$P-labeled probe or by examining the products using Southern blot analysis to corroborate predicted base pair size. Coordinate transcriptional/translational expression is demonstrated by sequential in situ RT-PCR/immunohistochemical analysis on serial tissue sections.

Fluorescence in situ hybridization (FISH) in combination with propidium iodide (PI) counterstaining is used to demonstrate mRNA expression of authentic and variant AFP in tissue sections. One suitable general method is described by Wulf, M., et al. Biotechniques, Vol. 19, No. 3, pp. 368-372, 1995.

After surgical removal, tissue samples are immediately fixed in 10% formaldehyde (pH 7.0) and nondecalcified, paraffin-embedded specimens are used for FISH. Pretreatment of sections before hybridization is carried out by covering the sections with 300 µl of prehybridization buffer (50% deionized formamide, 0.3 M NaCl, 10 mM Tris-HCl, pH 7.5; mM NaHPO.sub.4, pH 6.8; 5 mM EDTA; 0.1.times.Denhardt's, 10 mM dithiothreitol; 0.25 mg/ml yeast tRNA, 12.5% dextran sulfate; 0.5 mg/ml salmon sperm DNA and is incubated in a humid chamber for 2 hr at 42° C. For hybridization, digoxigenin-labeled double-stranded cDNA probe for the vAFP having the sequence 5-ACCATGAAGTGGGTGGAATC-3' (SEQ ID NO: 41)(ex 1S) and 5'-ATTTAAACTCCCAAAG-CAGCAC-3' (SEQ ID NO: 49)(ex-14A) are used. The probe is labeled with digoxigenin according to the protocol of the Dig-Labeling Kit (Boehringer Mannheim, Mannheim, Germany). Prior to hybridization, the labeled probe is mixed with prehybridization buffer to a concentration of 1 µg/mL, heated for 10 min. at 95° C. and quickly chilled on ice. Excess prehybridization buffer is removed from the slides, and approximately 30 µl of hybridization solution is applied to the sections. Sections are covered with a coverslip, sealed with rubber cement and hybridized in a humid chamber at 42.degree. C. for 18 h. The post-hybridization washing steps are performed as described by Weithege, T., et al. Pathol. Res. Pract., 187: 912-915, 1991.

Probe detection is carried-out using an anti-digoxigenin antibody conjugated to FITC (fluorescein isothiocyanate). Unbound conjugate is removed by washing two times for 10 min. with phosphate-buffered saline (PBS) (3.8 mM NaH$_2$PO$_4$; 7.8 mM Na$_2$ HPO$_4$; 0.13 M NaCl). Sections are counterstained with PI in PBS (500 ng/mL) for 5 min. at room temperature (30 µl per section). Excess PI is removed by washing with PBS, followed by dehydration (70%, 96%, 100% ethanol). Sections are air-dried and mounted in a glycerol/PBS solution. For analyses, a fluorescence microscope is used.

Using FISH, differential expression of the authentic AFP or vAFP mRNA in precancer and cancer cells is determined as compared to normal cells.

7.19. In Situ PCR and In Situ RT-PCR of Paraffin-Embedded Tissue Sections for Localization of Nucleic Acids of vAFP The following protocol is used to detect nucleic acids of AFP and vAFP which may be associated with precancer and cancer, in precancer and cancer cells. The method is also useful to detect the chromosomal location of the nucleic acid or chromosomal abnormalities at the location Cell Lines HepG2 and K562 cell lines are used in this study. Pellets of approximately 5×10$^6$ cells are washed in PBS, re-suspended in 1 ml of 2% NuSieve low melting-point agarose allowed to solidify, fixed for 2 hr in 4% paraformaldehyde or 10% formalin, and embedded in paraffin by routine histopathology techniques.

RNA Extraction

The guanidine isothiocyanate-cesium chloride method of Glisin et al (Biochemistry Vol. 13; 2633, 1974) is used to extract total RNA from the cell lines. Poly A+RNA from normal human brain, liver, thymus, stomach, and bone marrow are used.

Northern Blot

Standard formaldehyde gels were run with total RNA (10 µg/well) at 120 v. 100 mAmp for 3 hr. At the end of the run, the gels are washed for 15 min in 20×. SSC and then blotted overnight by capillary flow transfer onto a 0.45-.µ.m nitrocellulose filter. The blots are UV crosslinked at 1200 Joules and pre-hybridized for 4 hr. The Stratagene Prime-It kit (Stratagene; La Jolla, Calif.) is used to label the probe. The probes are prepared by random priming of inserts gel purified from restriction endonuclease digests of plasmids containing full-length cDNAs for vAFP with $^{32}$P-dCTP. Probe (1×10$^6$ cpm) is added to each ml of hybridizing buffer. After overnight hybridization, the blot is treated under the following stringent conditions: washed once in 2×SSC/0.1% SDS at room temperature, the blot is washed once in 2×SSC/0.1% at room temperature (RT; 30 min) and once with 0.1% SSC, 0.1% SDS at 60 C (30 min). The blots are then air-dried and autoradiographed at −80° C. on Kodak XAR5 film for 1-2 days.

Standard PCR

Oligonucleotide primers for vAFP are made using a MilliGen 8700 DNA synthesizer. Sequences are 5'-CTTC-CATATTGGATTCTTACCCAATG-3' (SEQ ID NO: 42)(ex-2S) and 5'-TAAACCCTGGTGTTGGCCAG-3' (SEQ ID NO: 47)(ex-12S). All buffers, enzymes, and nucleotides used are obtained from Applied Biosystems. PCR products are analyzed electrophoretically using a 1% agarose gel (80 V, 3 hr) and the ethidium bromide staining is observed under UV light, followed by Southern analysis with nested $^{32}$P-labeled probes.

Southern Analysis

Gels are denatured in 1.5 M NaCl/0.6 M NaOH and 1.5 M NaCl/2 M Tris and blotted onto a 0.2-μm nitrocellulose filter in 20×SSC by capillary flow transfer overnight. The filters are cross-linked at 80° C. under vacuum and put in hybridization buffer. Anti-sense nested probes are end-labeled by standard $^{32}$P procedures. Hybridization with the probe is done overnight at 42° C. Stringency washing at RT is in 5×SSC/0.1% SDS (twice for 30 min), then 1×SSC/0.1% SDS (twice for 30 min). Filters are air-dried and autoradiographed at −80° C. on Kodak XAR5 film for 2-4 hr.

In Situ PCR

The in situ PCR technique for localizing specific DNA sequences is performed by a three-step protocol. After dewaxing the tissue sections, a protein digestion is carried out to facilitate reagent penetration into the cells. A second step consists of the PCR itself with simultaneous labeling of the PCR products, followed by a third step that visualizes the labeled product. The in situ amplification technique for RNA detection utilizes a similar protocol. However, it incorporates two additional steps. After proteinase digestion the tissue is exposed to RNAse-free DNAse to avoid amplification of genomic DNA. Second, the remaining mRNA is reverse-transcribed to form cDNA templates, which are in turn amplified by PCR. To maximize the efficiency of the in situ PCR technique, all of these protocol steps must be optimized for individual analysis. The reverse transcription and the PCR steps is performed using an OmniSlide thermocycler (20-slide capacity) equipped with a heated wash module.

Protease Digestion

Depending on the fixative and the nature of the tissue, reagent access to the target nucleic acid can vary. Optimal permeability methods, can be obtained by varying the concentration of proteinase K between 1 and 100 μg/ml and incubation time (5-45 min).

DNAse Digestion

Deoxyribonuclease I Amplification Grade 10 U/slide is used to degrade the DNA according to standard methods. The influence of different digestion times on the quality of the staining is tested.

Reverse Transcription

For this step the SuperScript Preamplification System is used following standard methods. In summary, the sections are immersed in a solution containing the random primers, covered with parafilm coverslips, and incubated in the thermocycler for 10 min at 70° C. After removing the coverslips, another solution containing the reverse transcriptase (100 U/section) is added and covered with a new piece of parafilm. The slides are then maintained at RT for 10 min, at 45° C. for 45 min, and at 70° C. for 10 min.

PCR

Before the in situ PCR experiment, all parameters for the PCR reaction, including $MgCl_2$ concentration, pH, and annealing temperature, are optimized by standard PCR. At this point the PCR products can be cloned and sequenced to confirm identity. Optimization of conditions favoring single band production is advised because it is not possible to distinguish PCR products of different molecular weights in the tissue sections. To eliminate the possibility of generating PCR products from genomic DNA, it is important to design primers that bridge introns so as to distinguish template source on the basis of product size.

Synchronized "hot start" PCR is achieved using the Taq neutralizing antibody technique (Kellogg et al., Bio Techniques 6: 1134, 1994).

The following PCR mixture is used: 2.5 μM $MgCl_2$ 200 μM dNTP2, 100 μM digoxigenin-11-2'-deoxyuridine-5'-triphosphate, 1 ng/μl primers, 50 μM KCl, 10 μM Tris-HCL, pH 8.3. An 80-μl aliquot of solution is applied to each slide, and then each slide is covered by slanted glass coverslips, sealed with rubber cement, and placed in the thermocycler. The targets are amplified, 15-20 cycles to obtain crisp staining. After DNA amplification, two washes in 0.1×SSC at 45° C., 20 min each, are performed to eliminate unbound nucleotides.

Development of Digoxigenin

Detection of digoxigenin-tagged PCR products can be done with a kit standard in the art. It involves a 2-hr incubation with an anti-digoxigenin antibody bound to alkaline phosphatase. After a thorough rinse, the appropriate substrates (nitroblue tetrazolium and 5-bromo-chloro-3-indolyl-phosphate) are enzymatically transformed into a dark blue precipitate. Color deposition is checked under the microscope.

Polyvinyl alcohol can enhance the intensity of the alkaline phosphatase-nitroblue tetrazolium reaction and prevent diffusion of the precipitate. To take advantage of this technique the dilution of the anti-digoxigenin antibody is increased to 1:2000 (instead of the usual 1:500 recommended by the manufacturer) to obtain considerable background reduction.

Controls

The PCR technique is well known for its ability to amplify even single copies of DNA in a sample, contaminants included. Therefore, precautions that are recommended for routine PCR with regard to scrupulous care with cleanliness, use of a dedicated set of pipettes, and preparation of the PCR mixture away from the amplification area are also applicable for in situ PCR. In addition, working with tissue sections adds new concerns, such as heterogeneous application of reagents, bubbles, drying of the boundaries, and stability of the nucleic acids during the preparation of the samples.

At least three types of controls are recommended in every experiment to avoid false-positives or -negatives.

Positive Control

Include a section from a block that has previously been found positive for the same set of primers. If this is the first time that these primers are being used, a section of a well-fixed tissue or cell line known to have a high expression of the target nucleic acid as determined by other techniques (e.g., Northern analysis, standard PCR, in situ hybridization is included).

Negative Controls

Omission of the reverse transcription and/or RNAse treatment will yield information about nonspecific amplification of remaining nuclear or mitochondrial DNA.

Omission of the primers in the PCR mixture will reveal nonspecific staining due to endogenous priming: DNA fragments produced by the exonuclease activity of the DNA polymerase and other artifacts such as intrinsic alkaline phosphatase activity.

An additional control consists of establishing existing relationship between the transcriptional/translational products. This can be done by staining one section for the nucleic acid by in situ PCR and a serial section with a specific antibody against the polypeptide. The co-localization of the mRNA and its protein within the same cells will strengthen the validity of the observation, can be applied to authentic AFP.

Confirmation of the in situ PCR product integrity can be achieved in two ways: (a) It is possible to scrape the tissue of the glass slide after in situ PCR, to extract the DNA and to analyze by agarose gel electrophoresis and Southern blot with the appropriate radioactive probe. Cloning and sequencing of this product is also possible, after additional PCR cycles to yield products without modified bases, (b) Product identity is tested by performing in situ hybridization with a $^{32}$P-labeled nested probe after the amplification. This procedure can be used for indirect in situ PCR.

7.20. Variant AFP Expression in Fetal Tissues

The expression of vAFP by in situ hybridization in fetal tissue is evaluated to determine if these molecules were potentially involved in early organogenesis. This would establish vAFP as an oncofetal antigen and provide additional support for the hypothesis that vAFP is indicative of the process of carcinogenesis and fetal development. Multiple sections of human tissue from various stages of embryonal development and adult are evaluated.

Sections (4 μm thick) are mounted on slides coated with Vectabond, dewaxed and prepared for hybridization with RNA probes. In summary, the vAFP DNA fragment can be subcloned into a suitable vector and linearized with the appropriate restriction enzymes. Labeled probes are prepared using digoxigenin-11-UTP and T7 or T3 RNA polymerases to synthesize sense and antisense RNA transcripts, respectively. Hybridization is performed in a moist chamber at 46° C. for 20 hours in a 15-μl volume containing 0.5 ng/μl of probe for each section. Stringency washes included treatments with 150 mmol/L NaCl, 15 mmol/L sodium citrate, pH 7.0 (SSC), and sodium dodecyl sulfate (SDS) as follows: four washes in 2×SSC/0/1% SDS, two washes in 0.1×SSC/0.1% SDS at 46° C., brief rinses in 2×SSC, incubation in 2×SSC containing 10 μg/ml RNAse at 37° C. for 15 minutes, and additional rinses in 2×SSC.

Visualization of digoxigenin is performed with a monoclonal antibody coupled to alkaline phosphatase diluted about 1:500 acting for 2 hours at room temperature. Nitroblue tetrazolium chloride and 5-bromo-4-chloro-3-indoly-phosphate are used as substrates for the alkaline phosphatase. The use of the sense probe and treatment of the sections with RNAse before the hybridization are included.

7.21. Interpretation and Mechanistic Underpinnings of the Invention

The present invention identifies at least two variant forms of AFP expressed preferentially in hemopoietic progenitors, but not in mature blood cells or in hepatic cells. The invention is not limited by the mechanisms discussed. These results suggest that the AFP gene locus of chromatin in hemopoietic progenitor is open and accessible to transcription factors for the mRNA expression. In other words, chromatin-related repression of authentic AFP, which is a mechanism to block inappropriate expression of authentic AFP in non-endodermal cells, is incomplete in hemopoietic progenitors and allows vAFP to be transcribed. In the case of K562, strictly speaking, very small amounts of authentic AFP transcripts could be detected when the PCR cycles were increased (FIG. 5B). This indicates that K562 express vAFP at much higher level than authentic AFP. Conversely, vAFP could be detected in HepG2 by increasing cycles of RT-PCR. Therefore, our data taken from the cell lines suggest that three types of patterns are present with respect to the authentic and variant transcripts of AFP. Hepatic cells (HepG2) express authentic AFP dominantly, while hemopoietic cells (K562) express vAFP dominantly. Fibroblasts (MRC5) express neither authentic AFP nor vAFP. These results prompt two questions with respect to AFP expression. One is what is the mechanism of the opening of the AFP locus in the chromatin giving rise to whichever of the transcripts is expressed. The other is what is the transcriptional machinery associated with the different forms of transcripts.

The different usage of the first exon suggests the vAFP expression is dependent on the unique promotor. The mouse has proved an excellent model system for studying tissue-specific and developmentally regulated transcriptional control of authentic AFP in vivo as well as in vitro. Extensive studies have established that the transcriptional control of the AFP gene is mediated by five cis-acting regulatory domains, including the AFP promoter, three distinct enhancer elements and one repressor region located between the AFP promoter and the upstream enhancers. There are a number of transcription factors binding in the promotor region and involving the expression of the authentic AFP form. GATA4 could be a master gene for AFP gene expression and endodermal differentiation. In addition, GATA1 and GATA2 are indispensable factors for early hemopoietic differentiation. Interestingly, several possible GATA family binding sites are identified in the exon A genomic sequence as well as other transcription factor binding sites associated with hematopoiesis such as MZF-1 and AML-1. Thus, it is noteworthy to see whether these transcription factors expressed in hemopoietic progenitors are involved in the transcription of vAFP. Although there have been reports on the different promoters of the variant AFP transcripts in mouse and rat, there is no report about human variant AFP transcripts nor identification of exon A and exon B at 5' upstream of exon 1 in any species.

There is an explosion of studies about the possibility of transdifferentiation events in mammals. While evidence for the phenomenology is expanding rapidly, almost all of the evidence is inconclusive, and the approach to elucidate possible mechanism(s) is very limited. As a new model system, the AFP gene expression is ideal, because the gene is one of the most characterized in vivo and in vitro with respect to cell type-specific expression. A dynamic transition of the gene expression pattern could be measured by using gene array or gene tip technology if an in vitro conditional system with respect to the expression of different forms of AFP is developed. This approach could provide proof of transdifferentiation between hepatic and hemopoietic cells and be suggestive of a possible mechanism(s).

At present, apart from hemopoietic organs, brain is the only tissue in which vAFP expression is observed. Although there are claims that neural stem cells in the subventricular zone (SVZ) of the brain are able to differentiate to endodermal cells, the data are not yet conclusive. Therefore, the finding of vAFP+ cells in the brain is highly interesting and suggests, at the least, that cells in the brain possibly progenitors may share aspects of the developmental potential of endodermal progenitors just as CD34+Lin− hemopoietic progenitors do.

The function of the vAFP is unclear, because the amount of mRNA is extremely low and no protein products are found in assays using immuno-histochemistry with anti-AFP antibodies. In addition, there are no long open reading frame starts in exon A or B to connect exon 2 of authentic AFP if only ATG is considered as an initiation codon. In that case, an initiation codon at exon 3 would be used for the translation so that the translated product from vAFP transcripts would be a truncated form. However, since there are TTG and CTG in exon B to connect the open reading frame of exon 2, one of them could work as an alternative initiation codon.

We claim:

1. A method of detecting a variant form of alpha-fetoprotein (AFP) mRNA comprising:
   (a) combining a sample suspected of containing the variant form of AFP mRNA wherein the variant form of AFP cDNA comprises exons 1-14 of the cDNA encoding AFP in which exon 1 has been replaced by the polynucleotide sequence of exon A (SEQ ID NO:1), or a fusion of exon A and exon B (SEQ ID NO:2) with:
      (i) a forward primer capable of hybridizing to the exon A (SEQ ID NO:1) or the fusion of exon A and exon B (SEQ ID NO:2) of the cDNA encoding the variant AFP,
      (ii) a reverse primer that is at least 10 nucleotides long and corresponds to a sequence from AFP exons 2-14: and
      (iii) reagents for PCR to form a mixture,
   (b) subjecting the mixture to thermocycling, and
   (c) determining the absence or the presence of the cDNA corresponding to at least a portion of the variant form of AFP mRNA in the thermocycled mixture,
   wherein the presence of the cDNA indicates that the sample comprises the variant form of AFP.

2. The method of claim 1 in which the forward primer comprises SEQ ID NOS: 41, 42, 47, 51, 52, or complements thereof.

3. The method of claim 1 in which the forward primer comprises SEQ ID NO:51, SEQ ID NO:52, or a complement thereof and the reverse primer comprises SEQ ID NO:49, or a complement thereof.

4. A method for detecting a polynucleotide of a variant form of alpha-fetoprotein (AFP), the method comprising:
   (a) combining a sample suspected of containing the variant form of AFP mRNA wherein the variant form of AFP cDNA comprises exons 1-14 of the cDNA encoding AFP in which exon 1 of the cDNA encoding AFP has been replaced by the polynucleotide sequence of exon A (SEQ ID NO:1), or a fusion of exon A and exon B (SEQ ID NO:2) with a nucleic acid capable of hybridizing to exon A (SEQ ID NO:1) or a fusion of exon A and exon B (SEQ ID NO:2);
   (b) detecting the absence or the presence of a hybridization complex in the sample wherein the hybridization complex comprises the nucleic acid and indicates the presence of the variant form of AFP in the sample.

5. The method of claim 4 in which the mRNA in the sample is amplified by PCR prior to hybridization.

* * * * *

SEQUENCE LISTING

<160> NUMBER OF SEQ IDS NOS: 72

<210> SEQ ID NO 1
<211> LENGTH: 197
<212> TYPE: DNA
<213> ORGANISM: Homo sapiens

<400> SEQUENCE: 1

```
tttcttaaga attaagggac agactatggg ctggaggact ttgaggatgt ctgtctcata      60
acacttgggt tgtatctgtt ctatggggct tgttttaagc ttggcaactt gcaacagggt     120
tcactgactt tctccccagg cccaagcttc catattggat tcttaccaat gtactgcaga    180
gataagttta gctgacc                                                    197
```

<210> SEQ ID NO 2
<211> LENGTH: 317
<212> TYPE: DNA
<213> ORGANISM: Homo sapiens

<400> SEQUENCE: 2

```
gactatgggc tggaggactt tgaggatgtc tgtctcataa cacttgggtt gtatctgttc      60
tatgggcttt gttttaagct tggcaacttg caacagggtt cactgacttt ctccccaggc    120
ccaaggtatt ccttcataac aaatactttg gctttcatat atttgagtaa agtccccctt    180
gaggaagagt agaagaactg cactttgtaa atactatcct ggaatccaaa cggatagaca    240
aggatggtgc tacctctttc tggagacttc catattggat tcttaccaat gtactgcaga    300
gataagttta gctgacc                                                    317
```

<210> SEQ ID NO 3
<211> LENGTH: 197
<212> TYPE: DNA
<213> ORGANISM: Homo sapiens

<400> SEQUENCE: 3

```
tttcttaagg attaagggat agactatggg ctggaggact ttgaggatgt ctgtctcata      60
acacttgggt tgtatctgtt ctatggggct tgttttaagc ttggcaactt gcaacagggt     120
tcactgactt tctccccagg cccaagcttc catattggat tcttaccaat gtactgcaga    180
gataagttta gctgacc                                                    197
```

<210> SEQ ID NO 4
<211> LENGTH: 197
<212> TYPE: DNA
<213> ORGANISM: Homo sapiens

<400> SEQUENCE: 4

```
tttcttaaga attaagggac agactatgga ctggaggact ttgaggatgt ctgtctcata      60
acacttgggt tgtatctgtt ctatggggcc tgttttaagc ttggcaactt gcaacagggt    120
tcactgactt tctccccagg cccaagcttc catattggat tcttaccaat gtactgcaga    180
gataagttta gctgacc                                                    197
```

<210> SEQ ID NO 5
<211> LENGTH: 195
<212> TYPE: DNA
<213> ORGANISM: Homo sapiens

<400> SEQUENCE: 5

```
tttcttaaga attaagggac agactatggg ctggaggact ttgaggatgt ctgtctcata      60
acacttgggt gtatctgttc tatgggctt gttttaagct tgcaacttgc aacagggttc     120
actgactttc tccccaggcc caagcttcca tattggattc ttaccaatgt actgcagaga    180
taagtttagc tgacc                                                      195

<210> SEQ ID NO 6
<211> LENGTH: 199
<212> TYPE: DNA
<213> ORGANISM: Homo sapiens

<400> SEQUENCE: 6
tttcttaaga attaagggac agactatggg ctggaggact ttgaggatgt ctgtctcata      60
acacttgggt tgtatctgtt ctatggtggc ttgttttaag cttggcaact tgcaacaggg    120
ttccactgac tttctcccca ggcccaagct tccatattgg attcttacca atgtactgca    180
gagataagtt tagctgacc                                                  199

<210> SEQ ID NO 7
<211> LENGTH: 197
<212> TYPE: DNA
<213> ORGANISM: Homo sapiens

<400> SEQUENCE: 7
tttcttaaga attaagggac agactatgga ctggaggact ttgaggatgt ctgtttcata      60
acacttgggt tgtatctgtt ctatggggcc tgttttaagc ttggcagctt gcaacagggt    120
tcattgactt tctccctagg cccaagcttc catattggat tcttaccaat gtactgcaga    180
gataagttta gctgacc                                                    197

<210> SEQ ID NO 8
<211> LENGTH: 197
<212> TYPE: DNA
<213> ORGANISM: Homo sapiens

<400> SEQUENCE: 8
tctcctaaga actaagggac agactacggg ctggaggact ctgaggatgc ctgtcccata      60
acactcgggt tgcatctgct ctacgggct tgcttcaagc ttggcaacct gcaacagggt     120
ccactgactc tctccccagg cccaagcctc catactggat ccttaccaac gtactgcaga    180
gataagttta gctgacc                                                    197

<210> SEQ ID NO 9
<211> LENGTH: 197
<212> TYPE: DNA
<213> ORGANISM: Homo sapiens

<400> SEQUENCE: 9
tctcctaaaa actaaagaac agactacaga ctgaagaact ctgaagatac ctgtcccata      60
acactcagat tgcatctact ctacgagact tgcttcaaac ttgacaacct gcaacaagat    120
ccactgactc tctccccaag cccaaacctc catactggat ccttaccaac gtactgcaga    180
gataagttta gctgacc                                                    197

<210> SEQ ID NO 10
<211> LENGTH: 317
<212> TYPE: DNA
<213> ORGANISM: Homo sapiens

<400> SEQUENCE: 10
```

```
gactatgggc tggaggactt tgaggatgtc tgtctcataa cacttgggtt gtatctgttc    60 tatgggctc gttttaagct tggcaacttg caacagggtt cactgactt tctccccaggc    120 ccaaggtatc ccttcataac aaatactttg gctttcatat atttgagtaa agtcccccttc   180 gaggaagaat agaagaactg cactttgtaa atactatcct ggaatccaaa cggatagaca    240
aggatggtgc tacctctttc tggagacttc catattggat tcttaccaat gtactgcaga    300
gataagttta gctgacc                                                   317
```

```
<210> SEQ ID NO 11
<211> LENGTH: 317
<212> TYPE: DNA
<213> ORGANISM: Homo sapiens

<400> SEQUENCE: 11
gactatgggc tggaggactt tgaggatgtc tgtctcataa cacttgggtt atatctgttc    60 tatgggctt gttttaagct tggcaacttg caacagggtt cactgactt tctccccaggc    120 ccaaggtatt ccttcataac aaatactttg gctttcatat atttgagtaa agtccccct    180 gaggaagagt agaagaactg cactttgtaa atactatcct ggaatccaaa tggatagaca    240
aggatggtgc tacctctttc tggagacttc catattggat tcttaccaat gtactgcaga    300
gataagttta gctgacc                                                   317
```

```
<210> SEQ ID NO 12
<211> LENGTH: 314
<212> TYPE: DNA
<213> ORGANISM: Homo sapiens

<400> SEQUENCE: 12
gactatgggc tggaggactt tgaggatgtc tgtctcataa cacttgggtt gtatctgttc    60 tatgggctt gttttaagct tggcaacttg caacagggtt cactgactt tctccccaggc    120 ccaaggtatt ccttcataaa aatactttgg ctttcatata tttgagtaaa gtccccccttg   180 agaagagtag aagaactgca ctttgtaaat actatcctgg aatcaaacgg atagacaagg    240
atggtgctac ctctttctgg agacttccat attggattct taccaatgta ctgcagagat    300
aagtttagct gacc                                                      314
```

```
<210> SEQ ID NO 13
<211> LENGTH: 320
<212> TYPE: DNA
<213> ORGANISM: Homo sapiens

<400> SEQUENCE: 13
gactatgggc tggaggactt tgaggatgtc tgtctcataa cacttgggtt gtatctgtta    60
ctatggggct tgttttaagc ttggcaactt gcaacagggt tcactgactt tctccccagt    120
gcccaaggta ttccttcata acaaatactt tggctttcat atatttgagt aaagtccccc    180
ttgaggaaga gtagaagaac tgcactttgt aaatactatc tggaatccaa acggatagaa    240
caaggatggt gctacctctt tctggagact tccatattgg attcttacca atgttactgc    300
agagataagt ttagctgacc                                                320
```

```
<210> SEQ ID NO 14
<211> LENGTH: 317
<212> TYPE: DNA
<213> ORGANISM: Homo sapiens

<400> SEQUENCE: 14
```

```
gactatgggc tggaggactt tgaggatgtc tgtctcataa cacttgggtt atatctgttc     60
tatgggactt gtttcaagct tggtaacttg caacagggtt cactgacttt ctccccaggc    120
ccaaggtatt ccttcatgac aaatactttg gctttcatat atttgagtaa agtcccccct    180
gaggaagagt agaagaactg cactttgtaa atactatcct ggaatccaaa tggatagaca    240
aggatggtgc tacctctttc tggagacttc catattggat tcttaccagt gcactgcaga    300
gataagttta gctgacc                                                   317

<210> SEQ ID NO 15
<211> LENGTH: 317
<212> TYPE: DNA
<213> ORGANISM: Homo sapiens

<400> SEQUENCE: 15
gaccatgggc cggaggactc tgaggacgtc cgtcccataa cacctgggct gcatccgtcc     60
tacggggctc gtctcaagct cggcaactta caacagagtt cactaacttt ctccccagac    120
ccaagatatt ccttcataac aaatactttg actttcatat atttgaataa agtccccctt    180
aagaaagaat agaaaaactg cactttataa atactatcct gaaatccaaa cgaatagaca    240
aagatagtac tacctctttc tggagacttc catattggat tcttaccaat gtactgcaga    300
gataagttta gctgacc                                                   317

<210> SEQ ID NO 16
<211> LENGTH: 317
<212> TYPE: DNA
<213> ORGANISM: Homo sapiens

<400> SEQUENCE: 16
gaccatgggc cgggggggctc tgagggcgtc cgtcccatga cgcctgggct gcatccgtcc    60 tgcgggctc gtctcaggct cggcagctta cgacggagtt cgctagcttt ctccccaggc    120
ccaggatgtt ccttcatgac aaatactttg actttcatat atttgaataa agtctctctt    180
aagaaagaat agaaaaattg catttttataa atactattct gaaattcaaa tgaatagaca    240
aagatagtat tacttctttt tggagacttt catattggat ttttactaat gtactgtaga    300
gataagttta gctgatt                                                   317

<210> SEQ ID NO 17
<211> LENGTH: 339
<212> TYPE: DNA
<213> ORGANISM: Homo sapiens
<220> FEATURE:
<221> NAME/KEY: CDS
<222> LOCATION: (1)..(12)
<220> FEATURE:
<221> NAME/KEY: CDS
<222> LOCATION: (16)..(210)
<220> FEATURE:
<221> NAME/KEY: CDS
<222> LOCATION: (214)..(228)
<220> FEATURE:
<221> NAME/KEY: CDS
<222> LOCATION: (232)..(255)
<220> FEATURE:
<221> NAME/KEY: CDS
<222> LOCATION: (259)..(333)
<220> FEATURE:
<221> NAME/KEY: CDS
<222> LOCATION: (337)..(339)

<400> SEQUENCE: 17 ttt ctt aag aat taa ggg aca gac tat ggg ctg gag gac ttt gag gat     48
Phe Leu Lys Asn     Gly Thr Asp Tyr Gly Leu Glu Asp Phe Glu Asp
```

```
                1               5                  10                 15
gtc tgt ctc ata aca ctt ggg ttg tat ctg ttc tat ggg gct tgt ttt       96
Val Cys Leu Ile Thr Leu Gly Leu Tyr Leu Phe Tyr Gly Ala Cys Phe
                        20                 25                 30 aag ctt ggc aac ttg caa cag ggt tca ctg act ttc tcc cca ggc cca      144
Lys Leu Gly Asn Leu Gln Gln Gly Ser Leu Thr Phe Ser Pro Gly Pro
                35                 40                 45 agg tat tcc ttc ata aca aat act ttg gct ttc ata tat ttg agt aaa      192
Arg Tyr Ser Phe Ile Thr Asn Thr Leu Ala Phe Ile Tyr Leu Ser Lys
            50                 55                 60 gtc ccc ctt gag gaa gag tag aag aac tgc act ttg taa ata cta tcc      240
Val Pro Leu Glu Glu Glu     Lys Asn Cys Thr Leu     Ile Leu Ser
65                     70                     75 tgg aat cca aac gga tag aca agg atg gtg cta cct ctt tct gga gac      288
Trp Asn Pro Asn Gly     Thr Arg Met Val Leu Pro Leu Ser Gly Asp
            80                     85                 90 ttc cat att gga ttc tta cca atg tac tgc aga gat aag ttt agc tga      336
Phe His Ile Gly Phe Leu Pro Met Tyr Cys Arg Asp Lys Phe Ser
            95                 100                105 cct                                                                  339
Pro

<210> SEQ ID NO 18
<211> LENGTH: 4
<212> TYPE: PRT
<213> ORGANISM: Homo sapiens

<400> SEQUENCE: 18

Phe Leu Lys Asn
  1

<210> SEQ ID NO 19
<211> LENGTH: 65
<212> TYPE: PRT
<213> ORGANISM: Homo sapiens

<400> SEQUENCE: 19

Gly Thr Asp Tyr Gly Leu Glu Asp Phe Glu Asp Val Cys Leu Ile Thr
  1               5                  10                  15

Leu Gly Leu Tyr Leu Phe Tyr Gly Ala Cys Phe Lys Leu Gly Asn Leu
                20                  25                  30

Gln Gln Gly Ser Leu Thr Phe Ser Pro Gly Pro Arg Tyr Ser Phe Ile
            35                  40                  45

Thr Asn Thr Leu Ala Phe Ile Tyr Leu Ser Lys Val Pro Leu Glu Glu
        50                  55                  60

Glu
 65

<210> SEQ ID NO 20
<211> LENGTH: 5
<212> TYPE: PRT
<213> ORGANISM: Homo sapiens

<400> SEQUENCE: 20

Lys Asn Cys Thr Leu
  1               5

<210> SEQ ID NO 21
<211> LENGTH: 8
<212> TYPE: PRT
<213> ORGANISM: Homo sapiens
```

```
<400> SEQUENCE: 21

Ile Leu Ser Trp Asn Pro Asn Gly
1               5

<210> SEQ ID NO 22
<211> LENGTH: 25
<212> TYPE: PRT
<213> ORGANISM: Homo sapiens

<400> SEQUENCE: 22

Thr Arg Met Val Leu Pro Leu Ser Gly Asp Phe His Ile Gly Phe Leu
1               5                  10                  15

Pro Met Tyr Cys Arg Asp Lys Phe Ser
            20                  25

<210> SEQ ID NO 23
<211> LENGTH: 1
<212> TYPE: PRT
<213> ORGANISM: Homo sapiens

<400> SEQUENCE: 23

Pro
1

<210> SEQ ID NO 24
<211> LENGTH: 19
<212> TYPE: PRT
<213> ORGANISM: Homo sapiens

<400> SEQUENCE: 24

Phe Leu Arg Ile Lys Gly Gln Thr Met Gly Trp Arg Thr Leu Arg Met
1               5                  10                  15

Ser Val Ser

<210> SEQ ID NO 25
<211> LENGTH: 21
<212> TYPE: PRT
<213> ORGANISM: Homo sapiens

<400> SEQUENCE: 25

His Leu Gly Cys Ile Cys Ser Met Gly Leu Val Leu Ser Leu Ala Thr
1               5                  10                  15

Cys Asn Arg Val His
            20

<210> SEQ ID NO 26
<211> LENGTH: 10
<212> TYPE: PRT
<213> ORGANISM: Homo sapiens

<400> SEQUENCE: 26

Leu Ser Pro Gln Ala Gln Gly Ile Pro Ser
1               5                  10

<210> SEQ ID NO 27
<211> LENGTH: 8
<212> TYPE: PRT
<213> ORGANISM: Homo sapiens

<400> SEQUENCE: 27

Gln Ile Leu Trp Leu Ser Tyr Ile
1               5
```

```
<210> SEQ ID NO 28
<211> LENGTH: 49
<212> TYPE: PRT
<213> ORGANISM: Homo sapiens

<400> SEQUENCE: 28

Val Lys Ser Pro Leu Arg Lys Ser Arg Arg Thr Ala Leu Cys Lys Tyr
1               5                   10                  15

Tyr Gly Ile Gln Thr Asp Arg Gln Gly Trp Cys Tyr Leu Phe Leu Glu
            20                  25                  30

Thr Ser Ile Leu Asp Ser Tyr Gln Cys Thr Ala Glu Ile Ser Leu Ala
        35                  40                  45

Asp

<210> SEQ ID NO 29
<211> LENGTH: 1
<212> TYPE: PRT
<213> ORGANISM: Homo sapiens

<400> SEQUENCE: 29

Ser
 1

<210> SEQ ID NO 30
<211> LENGTH: 11
<212> TYPE: PRT
<213> ORGANISM: Homo sapiens

<400> SEQUENCE: 30

Glu Leu Arg Asp Arg Leu Trp Ala Gly Gly Leu
1               5                   10

<210> SEQ ID NO 31
<211> LENGTH: 17
<212> TYPE: PRT
<213> ORGANISM: Homo sapiens

<400> SEQUENCE: 31

Gly Cys Leu Ser His Asn Thr Trp Val Ser Val Leu Trp Gly Leu
1               5                   10                  15

Phe

<210> SEQ ID NO 32
<211> LENGTH: 30
<212> TYPE: PRT
<213> ORGANISM: Homo sapiens

<400> SEQUENCE: 32

Ala Trp Gln Leu Ala Thr Gly Phe Thr Asp Phe Leu Pro Arg Pro Lys
1               5                   10                  15

Val Phe Leu His Asn Lys Tyr Phe Gly Phe His Ile Phe Glu
            20                  25                  30

<210> SEQ ID NO 33
<211> LENGTH: 3
<212> TYPE: PRT
<213> ORGANISM: Homo sapiens

<400> SEQUENCE: 33

Ser Pro Pro
 1

<210> SEQ ID NO 34
```

```
<211> LENGTH: 39
<212> TYPE: PRT
<213> ORGANISM: Homo sapiens

<400> SEQUENCE: 34

Gly Arg Val Glu Glu Leu His Phe Val Asn Thr Ile Glu Ser Lys Arg
 1               5                  10                  15

Ile Asp Lys Asp Gly Ala Thr Ser Phe Trp Arg Leu Pro Tyr Trp Ile
            20                  25                  30

Leu Thr Asn Val Leu Gln Arg
        35

<210> SEQ ID NO 35
<211> LENGTH: 1
<212> TYPE: PRT
<213> ORGANISM: Homo sapiens

<400> SEQUENCE: 35

Val
 1

<210> SEQ ID NO 36
<211> LENGTH: 2
<212> TYPE: PRT
<213> ORGANISM: Homo sapiens

<400> SEQUENCE: 36

Leu Thr
 1

<210> SEQ ID NO 37
<211> LENGTH: 146
<212> TYPE: DNA
<213> ORGANISM: Homo sapiens

<400> SEQUENCE: 37
tttcttaaga attaagggac agactatggg ctggaggact tgaggatgt ctgtctcata      60 acacttgggt tgtatctgtt ctatggggct tgttttaagc ttggcaactt gcaacagggt    120
tcactgactt tctccccagg cccaag                                         146

<210> SEQ ID NO 38
<211> LENGTH: 73
<212> TYPE: DNA
<213> ORGANISM: Homo sapiens

<400> SEQUENCE: 38
cttccatatt ggattcttac caatgtactg cagagataag tttagctgac ctggctacca     60
tattttttgc cca                                                        73

<210> SEQ ID NO 39
<211> LENGTH: 339
<212> TYPE: DNA
<213> ORGANISM: Homo sapiens

<400> SEQUENCE: 39
gactatgggc tggaggactt tgaggatgtc tgtctcataa cacttgggtt gtatctgttc     60 tatgggctt gttttaagct tggcaacttg caacagggtt cactgacttt ctccccaggc    120
ccaaggtatt ccttcataac aaatactttg ctttcatat atttgagtaa agtccccctt    180
gaggaagagt agaagaactg cactttgtaa atactatcct ggaatccaaa cggatagaca    240
aggatggtgc tacctctttc tggagacttc catattggat tcttaccaat gtactgcaga    300
```

```
gataagttta gctgacctgg ctaccatatt ttttgccca                          339
```

<210> SEQ ID NO 40
<211> LENGTH: 840
<212> TYPE: DNA
<213> ORGANISM: Homo sapiens

<400> SEQUENCE: 40

```
gcagcaaatg ggaaaggtga agtcttgtac tctagagcat gattcaaata gataggctca    60
aattaaacaa atggagggat agtttgttct gcctaaaagc agtaatagga ggggaatcta   120
gaagctgggt ctggatggga agacattaag aaaggagagg gagagagagc aagcaagaag   180
gaggccggtc agggctctac aagaagagag tcaggtggta ttgatacgag tggaaaagat   240
cttttatgt tttatgccta gttccttgat acaaacttgt ggtgggggt tcttgaaaaa     300
gtgattgggg actatctgat ctggggttta gggcagggaa gaaacagcat gtaaaggaga   360
aaagacagag catttgttaa agagaattta acagcaagag gaaataagaa ccaatgatac   420
caaggataaa cgcagtcctt aactccccta tcactgaatt cttagaaata tgggggtagg   480
ggtggtggtg gtaattctgt tttctcccca taggtgagat aagcattggg ttaaatgtgc   540
tttctctctc tccctctcct ttcttaagaa ttaagggaca gactatgggc tggaggactt   600
tgaggatgtc tgtctcataa cacttgggtt gtatctgttc tatggggctt gttttaagct   660
tggcaacttg caacagggtt cactgacttt ctccccaggc ccaaggtact gtcctctttt   720
catatctgtt tgggccctc tggggcttga atatctgaga aaatataaac atttcaataa    780
tgttctgtgg tgagatgagt atgagagatg tgtcattcat ttgtatcaat gaatgaatga   840
```

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41

```
accatgaagt gggtggaatc                                                20
```

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42

```
cttccatatt ggattcttac caatg                                          25
```

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43

```
ggctaccata tttttgccc ag                                              22
```

<210> SEQ ID NO 44

```
-continued

<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ctacctgcct ttctggaaga ac                                              22

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gagatagcaa gaaggcatcc c                                               21

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
aaagaattaa gagaaagcag cttg                                            24

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
taaaccctgg tgttggccag                                                 20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cctgaagact gttcatctcc                                                 20

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
atttaaactc ccaaagcagc ac                                              22

<210> SEQ ID NO 50
<211> LENGTH: 24
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 50
agaattaagg gacagactat gggc                                        24

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gatgtctgtc tcataacact tggg                                        24

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
taagcttggc aacttgcaac aggg                                        24

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
atattgtgct tccaccactg cc                                          22

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tgcaaggccg gcttcgcggg c                                           21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tccttctgca tcctgtcggc a                                           21

<210> SEQ ID NO 56
<211> LENGTH: 22
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 56
tcatgagtct tgacaacaac gg                                              22

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cagccaccac gtgttgtctt gc                                              22

<210> SEQ ID NO 58
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
actagttagc ggccgcactg ggccccccccc cccccc                              36

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
actagttagc ggccgcactg gg                                              22

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ctcacctatt ccatattcat ttc                                             23

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ggtcagctaa acttatctct gc                                              22

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 62
ggcttcttga acaaactggg c                                          21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gctgcagcag tctgaatgtc c                                          21

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
attctgtttt caccccatag gtg                                        23

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tttctcagat attcaagccc cag                                        23

<210> SEQ ID NO 66
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cttccatatt ggattcttac ccaatg                                     26

<210> SEQ ID NO 67
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: region selected from the group consisting of
      aa, ac, ag, at, ax, ca, cc, cg, ct, cx, ga, gc, gg, gt, gx,
      ta, tc, tg, tt, tx, xa, xc, xg, xt, and xx, wherein
      "x" represents no residue.
<220> FEATURE:
<221> NAME/KEY: modified_base
<222> LOCATION: (11)..(12)
<223> OTHER INFORMATION: region selected from the group consisting of
      aa, ac, ag, at, ax, ca, cc, cg, ct, cx, ga, gc, gg, gt, gx,
      ta, tc, tg, tt, tx, xa, xc, xg, xt, and xx, wherein
      "x" represents no residue.
```

```
<400> SEQUENCE: 67
nnccaagctt nn                                                                12

<210> SEQ ID NO 68
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: region selected from the group consisting of
      aa, ac, ag, at, ax, ca, cc, cg, ct, cx, ga, gc, gg, gt, gx,
      ta, tc, tg, tt, tx, xa, xc, xg, xt, and xx, wherein
      "x" represents no residue.
<220> FEATURE:
<221> NAME/KEY: modified_base
<222> LOCATION: (11)..(12)
<223> OTHER INFORMATION: region selected from the group consisting of
      aa, ac, ag, at, ax, ca, cc, cg, ct, cx, ga, gc, gg, gt, gx,
      ta, tc, tg, tt, tx, xa, xc, xg, xt, and xx, wherein
      "x" represents no residue.

<400> SEQUENCE: 68
nnccaaggta nn                                                                12

<210> SEQ ID NO 69
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: region selected from the group consisting of
      aa, ac, ag, at, ax, ca, cc, cg, ct, cx, ga, gc, gg, gt, gx,
      ta, tc, tg, tt, tx, xa, xc, xg, xt, and xx, wherein
      "x" represents no residue.
<220> FEATURE:
<221> NAME/KEY: modified_base
<222> LOCATION: (11)..(12)
<223> OTHER INFORMATION: region selected from the group consisting of
      aa, ac, ag, at, ax, ca, cc, cg, ct, cx, ga, gc, gg, gt, gx,
      ta, tc, tg, tt, tx, xa, xc, xg, xt, and xx, wherein
      "x" represents no residue.

<400> SEQUENCE: 69
nnggagactt nn                                                                12

<210> SEQ ID NO 70
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
cccaagcttc                                                                   10

<210> SEQ ID NO 71
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 71
cccaaggtat                                                          10

<210> SEQ ID NO 72
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tggagacttc                                                          10
```